United States Patent [19]

Meruelo et al.

[11] Patent Number: 5,514,714
[45] Date of Patent: May 7, 1996

[54] METHODS AND POLYCYCLIC AROMATIC COMPOUND CONTAINING COMPOSITIONS FOR TREATING T-CELL-MEDIATED DISEASES

[75] Inventors: Daniel Meruelo, Scarborough, N.Y.;
Gad Lavie, Tenafly, N.J.

[73] Assignee: New York University, New York, N.Y.

[21] Appl. No.: 39,790

[22] Filed: Mar. 30, 1993

Related U.S. Application Data

[63] Continuation-in-part of Ser. No. 784,952, Nov. 1, 1991, abandoned, which is a continuation-in-part of Ser. No. 572,085, Aug. 23, 1990, abandoned.

[51] Int. Cl.$^6$ .................... A61K 31/195; A61K 31/19; A61K 31/12
[52] U.S. Cl. .................. 514/561; 514/569; 514/680; 514/885
[58] Field of Search ................... 514/732, 734, 514/561, 569, 680, 885

[56] References Cited

U.S. PATENT DOCUMENTS 4,898,891  2/1990  Lavie et al. ............... 514/732

OTHER PUBLICATIONS

Meruelo et al, "Therapeutic Agents With . . . Pseudohypericin" Proc. Nat. Acad Sci., U.S.A., vol. 85, pp. 5230–5234, Jul. 1988.

The Merck Manual; Merck & Co Inc., Fourteenth Editon pp. 1214, 1354 (1982).

*Primary Examiner*—Raymond Henley, III
*Attorney, Agent, or Firm*—Browdy and Neimark

[57] ABSTRACT

T cell-mediated diseases in mammals are treated using compositions comprising a polycyclic aromatic compound, preferably hypericin or pseudohypericin, and related compounds, including isomers, analogs, derivatives, salts, or ion pairs of hypericin or pseudohypericin. The above composition may be administered in combination with an immunosuppressive agent. Pharmaceutical compositions useful for treating a T cell-mediated disease comprise the above polycyclic aromatic compound, alone or in combination with an immunosuppressive agent. The compositions and methods are useful in treating diseases which include multiple sclerosis, myasthenia gravis, scleroderma, polymyositis, graft-versus-host disease, graft rejection, Graves disease, Addison's disease, autoimmune uveoretinitis, autoimmune thyroiditis, pemphigus vulgaris and rheumatoid arthritis. Psoriasis and systemic lups erythematosus. Also provided are methods for diminishing the expression of CD4 Molecules on the surface of a T lymphocyte, and for inducing multidrug resistance in a cell, comprising incubating the cell with an effective concentration of a polycyclic aromatic compound.

6 Claims, 9 Drawing Sheets

METHODS AND POLYCYCLIC AROMATIC COMPOUND CONTAINING COMPOSITIONS FOR TREATING T-CELL-MEDIATED DISEASES

This application is a continuation in part of U.S. patent application Ser. No. 07/784,952, filed Nov. 01, 1991, now abandoned which is a continuation in part of U.S. patent application Ser. No. 07/572,085, filed Aug. 23, 1990, now abandoned, which applications are herein entirely incorporated by reference.

BACKGROUND OF THE INVENTION

1. Field of the Invention

This invention pertains to the administration of polycyclic aromatic compounds for the treatment of T cell-mediated diseases in mammals and compositions useful for treating T cell-mediated diseases.

2. Description of the Background Art

T cell-mediated diseases have been characterized by the induction of cytotoxic T-lymphocytes expressing the CD8 antigen on their cell surface and/or helper T cells expressing the CD4 antigen on their cell surface. These diseases, non-limiting examples being graft-versus-host diseaser graft rejection, and autoimmune disorders, such as multiple sclerosis, rheumatoid arthritis, Graves diseases Addison's diseases polymyositis, insulin dependent diabetes, primary biliary cirrhosis, systemic Lupus erythematosus, psoriasis, scleroderma, represent a large number of host immune system disorders.

Graft-versus-host disease may occur when cells of the immune system such as stem cells or lymphocytes are transplanted into an allogeneic host, such as one genetically different at the major histocompatibility complex, which encodes cell surface antigens that give rise to strong immunological reactions. Transplants of cells of the immune system are made for treating certain forms of leukemia, aplastic anemia, and various immunodeficiency diseases. In order to prevent rejection of the foreign cells, the host is typically immunosuppressed, as with irradiation and/or immunosuppressive drugs. The transplanted immunocompetent cells recognize the host as foreign and mount an immune response directed against the host. In humans, the clinical manifestations of this graft-versus-host disease include fever, rash, anorexia, nausea, vomiting and watery or bloody diarrhea, weight loss and death.

It has also been reported that transfusion associated graft-versus-host disease can occur in immunocompetent transfusion recipients (Anderson, K. C., et al., *New Eng. J. Med* 323: 315–321, 1990).

Recipients of allogeneic (same species) solid tissue or organ grafts are usually treated with cytotoxic drugs such as cyclophosphamide, and other immunosuppressive drugs such as cyclosporin A (CsA), FK-506 (Metcalfe, S. et al., *Transplantation* 49:798–802, 1990), and more recently, 15-deoxyspergualin (Amemiya, H. et al., *Transplantation* 49:337–343, 1990). These drugs suppress the immune response against the transplanted tissue and thereby help prevent graft rejection. CsA is known to inhibit the activation of T cells by inhibiting the production and/or the secretion of cytokines such as interleukin-1 (L1), interleukin-2 (IL2), tumor necrosis factor (TNF) and interferon gamma, substances which are involved in the activation of cytotoxic T cells. Use of CsA, cyclophosphamide, 15-deoxyspergualin and FK-506 is limited not only because of the various toxic effects, but also due to the "global" induced immunosuppression which can lead to various infections and/or malignancyo Indeed, CsA therapy can result in the appearance of tumors, particularly lymphomas, in the treated host, necessitating discontinuance of therapy. CsA is also suspected to cause diabetes (Wahlstrom, M. E. et al., *Transplantation* 49:600–604, 1990). However CsA and FK-506 continue to be the most effective immunosuppressive therapy despite its dangerous side effects, due to a lack of other immunosuppressive agents that are as effective with less side effects.

Other approaches to treating allograft rejection involve the administration of monoclonal antibodies such as OKT3, which are specific for the $T_3$ molecule associated with the T cell receptor on all T lymphocytes including cytotoxic T cells (*New Engo J. Med.* 313:338, 1986). OKT3 treatment eliminates the T-effector cells which mediate this reaction.

An autoimmune disease results from a malfunction or misdirection of the immune system. In a subject afflicted with an autoimmune disease, the immune system often does not distinguish between self and foreign antigens, resulting in recognition of autologous tissues or soluble molecules as if they were foreign, and subsequent immune responses to autologous cells or tissue cause autologous tissue distruction or inflammatory reactions normally reserved for foreign organisms, pathogens, cells or tissue.

Current treatments for autoimmune diseases also involve administration of drugs which non-specifically suppress the immune response. Examples of such drugs include methotrexate, cyclophosphamide, azathioprine, FK-506 and cyclosporin A. Glucocorticosteroids, such as prednisone and methylprednisolone are also commonly employed to treat autoimmunity. These drugs have limited efficacy against autoimmune diseases, have toxic side effects and tend to induce a "global" immunosuppression.

Another approach for treating autoimmune diseases involves induction of immunological tolerance or antigen-specific suppression by oral administration of the particular autoantigen involved in the disease. Examples include oral administration of collagen for collagen-induced arthritis (Nagler-Anderson et al. (*Proc. Nat. Acad. Sci USA* 83:7443–7446, 1986); oral administration of myelin basic protein to treat experimental allergic encephalomyelitis (Higgins, P. et al., *J. Immunol.* 140:1440–1445, 1988). However, this approach is limited due to the difficulty in identifying and purifying the antigen(s) responsible for the autoimmune disease.

Hypericin and related polycyclic aromatic compounds, generally of plant origin, are known to be useful in treating variety of diseases that are caused by viruses and retroviruses.

U.S. Pat. No. 4,898,891 (Feb. 6, 1990) discloses the antiviral activity of two aromatic polycyclic dione compounds, hypericin and pseudohypericin and related compounds.

The assignee's U.S. patent application Ser. No. 07/328, 767, filed Mar. 20, 1989, as a continuation-in-part of U.S. patent application Ser. No. 07/084,008, filed Aug. 10, 1987 (now abandoned) expands upon the disclosure of U.S. Pat. No. 4,898, 891, which applications are entirely incorporated herein by reference, and disclose the use of hypericin and pseudohypericin as effective anti-retroviral agents.

The assignee's U.S. patent application Ser. No. 07/326, 392, filed Mar. 28, 1989 as a continuation-in-part of U.S. patent application Ser. No. 07/172,065, filed Mar. 23, 1988 (now abandoned), which applications are entirely incorporated by reference herein, disclose antiretroviral compositions comprising effective amounts of hypericin and pseudohypericin in combination with nucleoside analogs such as azidothymidine (AZT), and describe methods for treating retroviral infections with such compositions.

The assignee's copending U.S. patent application Ser. No. 299,971, filed Jan. 19, 1989 and corresponding PCT Publication PCT/US90/00398 (Jul. 21, 1990), which applications are herein entirely incorporated by references disclose hypericin related compound containing compositions and methods for inactivating viruses and retroviruses present in bloods blood products and other body fluids and, more generally biological fluids, as well as articles useful for practicing such methods.

The assignee's U.S. patent application Ser. No. 07/417, 163, filed Oct. 4, 1989 as a continuation-in-part of U.S. patent application Ser. No. 07/324,177, filed Mar. 19, 1989 (now abandoned) and corresponding PCT Publication PCT/US90/04163, which applications are herein entirely incorporated by reference, disclose compositions comprising aromatic polycyclic antiviral compounds and methods for treating viral infections. The disclosed polycyclic aromatic compounds include hypericin and related polycyclic diones as well as homologs, isomers, derivative, salts and analogs of such polycyclic dione compounds and mixtures thereof for treating viral and retroviral infections.

The assignee's copending U.S. patent application Ser. No. 07/552,889, filed May 14, 1990, which is entirely incorporated herein by referenced discloses aqueous pharmaceutical formulations and compositions comprising water-dispersed polycyclic aromatic compounds with improved biological and/or physical properties and methods of use thereof in treating viral and retroviral diseases.

Heretofore, there has been no disclosure or suggestion of the effects of the polycyclic aromatic compounds on T lymphocytes or their activities, nor on the function of the immune system.

At the present time there is a well-recognized need for effective agents and methods for treating T cell-mediated diseases, wherein the agents have no or low toxicity to the treated subject, but are effective in treating a broad spectrum of T-cell-mediated diseases. It is to such agents and methods that the present invention is directed.

Citation of documents herein is not intended as an admission that any of the documents cited herein is pertinent prior art, or an admission that the cited documents is considered material to the patentability of any of the claims of the present application, All statements as to the date or representation as to the contents of these documents is based on the information available to the applicant and does not constitute any admission as to the correctness of the dates or contents of these documents.

SUMMARY OF THE INVENTION

It is an object of the present invention to provide hypericin and related polycyclic aromatic compounds, pharmaceutical compositions and methods that have no or low toxicity for the subject being treated, but that are effective in the treatment of T cell-mediated diseases.

The present inventors have discovered that hypericin and related polycyclic aromatic compounds are useful in the treatment of a wide variety of diseases which are mediated by T cells. The effectiveness of these compounds in treating T cell-mediated diseases is attributable to their ability to interfere with T cell function at one of its several stages, for example, by inhibiting the lyric phase of the cytotoxicity reaction and by lowering the surface expression of CD4 on T cells.

Thus, the present invention is directed to a method for treating a T cell-mediated disease in a mammal in need of such treatment, comprising administering to the mammal an effective amount of a hypericin related or polycyclic aromatic compound or a composition comprising such a compound.

Preferably, in this method, a hypericin related or polycyclic aromatic compound may be selected from the group consisting of at least one of hypericin, pseudohypericin, desmethyl hypericin, hypericin diacetate, hypericin hexaacetate, hypericin methyl ester, hypericin propyl esther, isopropyl desmethyl hypericin, butyl ester of hypericic acid, sodium hypericin, potassium hypericin lithium hypericin, hypericin-lysine, hypericin-glutamine, hypericin-ethylenediamine, hypericin-TRIS, or isomers, analogs, derivatives, salts, or ion pairs thereof, and mixtures thereof. More preferably, the compound is hypericin or pseudohypericin. Such hypericin related or polycyclic aromatic compounds may be in the form of a single compound, a mixture, a solution, an emulsion, a suspension, a cell culture, a plant extract (such as an extract of St. John's wort a species of the genus Hypericum), fermentation culture, cells, tissue, secretion and/or derivative or extract thereof, provided by chemical synthesis or isolation from an organism containing the polycyclic aromatic compound.

The present invention is further directed to a method for treating or preventing a T cell-mediated disease in a mammal which comprises administering to a mammal in need of such treating or preventing, a combination including:

(a) a compound selected from the group consisting of hypericin, pseudohypericin, and isomers, analogs, derivatives, salts, or ion pairs of hypericin or pseudohypericin, and (b) an immunosuppressive agents wherein the combined amounts of (a) and (b) are effective for treating or preventing the disease.

Preferred immunosuppressive agents in the above method include at least one of asteroid, cyclosporin A or analogs thereof, cyclophosphamide, methotrexate, rapamycin, prednisone8 methylprednisolone, OKT-3, FK-506, 15-deoxyspergualin, azathioprine, anti-CD-3 monoclonal antibodies, or mixtures thereof.

The above methods may be used to treat any T cell-mediated disease, preferably one selected from the group consisting of multiple sclerosis, myasthenia gravis, scleroderma, polymyositis, graft-versus-host disease, graft rejection, Graves disease, Addison's disease, autoimmune uveoretinitis, autoimmune thyroidiris, Pemphigus vulgaris, systemic lupus erythematosus, primary biliary cirrhosis, rheumatoid arthritis. In a preferred embodiment the method is used to prevent or treat graft-versus-host disease or graft rejection in any organ transplantation including kidney, pancreas, liver, heart, lung, etc. Another preferred embodiment the method is used to prevent tissue damage and reduce pain in rheumatoid arthritis and in Lupus erythematosis.

Also provided is a pharmaceutical composition useful for treating a T cell-mediated disease comprising a combination including:

(a) an amount of a compound selected from the group consisting of hypericin, pseudohypericin, and isomers, analogs, derivatives, salts, or ion pairs of hypericin or pseudohypericin; and (b) an amount of an immunosuppressive agent, wherein the combined amounts of (a) and (b) are effective to treat or prevent the T cell-mediated disease.

In the above composition, the compound is preferably a hypericin related compound or polycyclic aromatic compound selected from the group consisting of at least one of hypericin, pseudohypericin, desmethyl hypericin, hypericin diacetate, hypericin hexaacetate, hypericin methyl ester, hypericin propyl esther, isopropyl desmethyl hypericin, butyl ester of hypericic acid, sodium hypericin, potassium hypericin lithium hypericin, hypericin-lysine, hypericin-glutamine, hypericin-ethylenediamine, hypericin-TRIS, or isomers, analogs, derivatives, salts, ion pairs, or mixtures thereof. The immunosuppressive agent may preferably be selected from at least one of cyclosporin A, cyclophosphamide, methotrexate, a steroid, rapamycin, an anti-CD3 monoclonal antibody, prednisone, methylprednisolone, OKT-3, FK-506, 15-deoxyspergualin, azathioprine and mixtures thereof. A preferred composition further comprises a pharmaceutically-acceptable carrier or diluent.

The present invention is further directed to a method for inhibiting the lyric activity of cytotoxic T-lymphocytes and for diminishing the expression of CD4 molecules on the surface of a T lymphocyte comprising contacting the T lymphocyte with an effective concentration of a compound selected from the group consisting of a hypericin related compound, as described herein or as would be clear to one skilled in the art, based on the teaching and guidance presented for a period of time sufficient to diminish the expression.

Also provided is a method for inducing multidrug resistance in a cells comprising culturing the cell with an effective concentration of a hypericin related compound, for a period of time sufficient to induce the multidrug resistance.

A preferred compound in the above two methods is selected from the group consisting of hypericin, pseudohypericin, desmethyl hypericin, hypericin diacetate, hypericin hexaacetate, hypericin methyl ester, hypericin propyl esther, isopropyl desmethyl hypericin, butyl ester of hypericic acids sodium hypericin, potassium hypericin lithium hypericin, hypericin-lysine, hypericin-glutamine, hypericin-ethylenediamine, hypericin-TRIS, or isomers, analogs, derivatives, salts, ion pairs, or mixtures thereof. A more preferred compound is hypericin or pseudohypericin.

These and other aspects, advantages and embodiments of the present invention will be apparent to those of ordinary skill in the art in light of the following description, claims and drawings.

BRIEF DESCRIPTIONS OF THE DRAWINGS

DETAILED DESCRIPTION OF THE PREFERRED EMBODIMENTS

Figure 1:
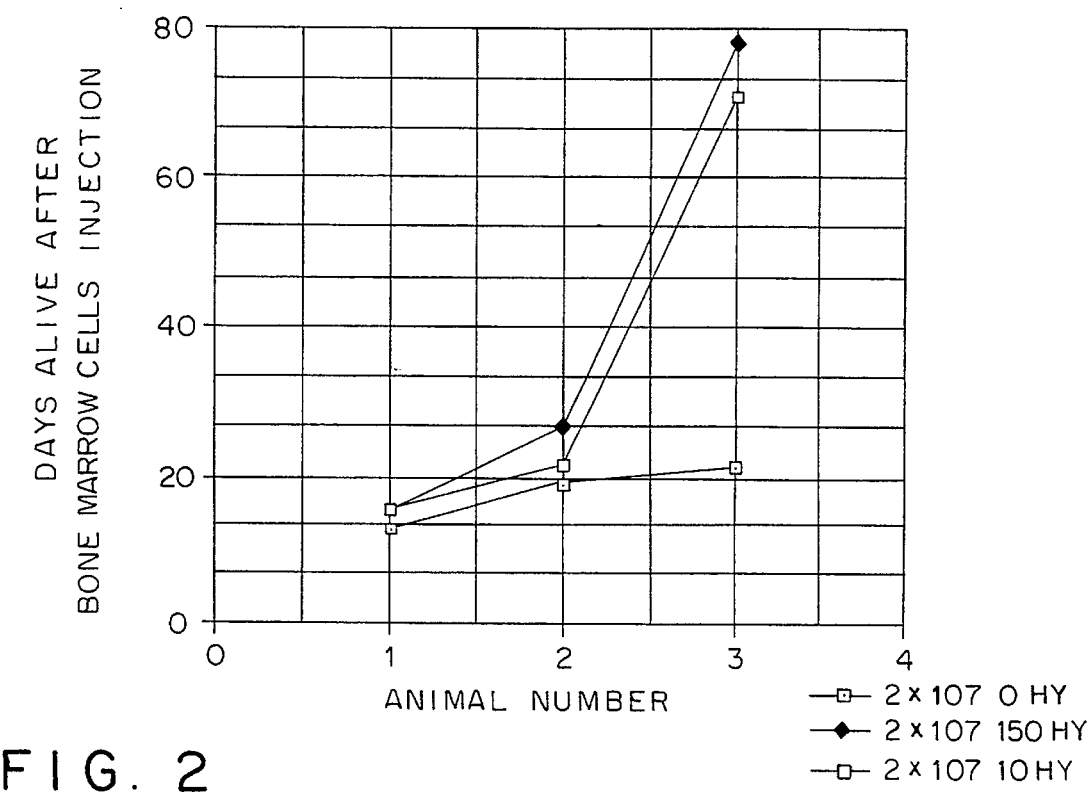
FIG. 1 is a graph showing the effect of hypericin administered 3 times a week on survival of mice with graft-versus-host disease (GVHD).

The present invention relates to compositions and methods which include at least one hypericin related compound which is useful in the inhibition of T lymphocyte lyric reactivity, diminution in the expression of CD4 on the surface of T cells, and in preventing, suppressing, or treating T cell-mediated diseases.

The present inventors have found that hypericin and related polycyclic aromatic compounds, as presented herein, can be used to diminish expression of CD4 on T cells and to treat a wide variety of diseases which are mediated by T cells. These findings are unexpected, as there have been no previous published reports that hypericin and related polycyclic aromatic compounds have any effects whatsoever on the immune system or on T cells themselves.

The compositions and methods of the present invention are useful in the treatment for the prevention of a wide variety of diseases which are partially or completely mediated by T cells and ameliorating the condition of the patients. Non-limiting examples of such diseases include graft-versus-host diseased graft rejection, autoimmune diseases mediated by T cells, and autoimmune diseases, such as multiple sclerosis, rheumatoid arthritis, myasthenia gravis, encephalomyelitis, Addison's disease, Graves' disease, scleroderma, polymyositis, insulin dependent diabetes mellitus, autoimmune uveoretinitis, systemic lupus erythematosus, inflammatory bowel disease including ulcerative colitis, pemphigus vulgaris, autoimmune thyroiditis, primary biliary cirrhosis, psoriatic arthritis, exfoliative psoriatic dermatitis, postular psoriasis, autoimmune hemolytic anemia, mixed connective tissue disease, autoimmune thrombocytopenic purpura, mixed connective tissue disease, polymyositis, Idiopathic Addison's disease, and other cell mediated inflammatory, granulomatous, degenerative and atrophic disorders. Se, e.g., Berkow et al., eds, supra, pages 303–364, 710–718, 1083, 1305–1377, 1338 1677–1684, and 2435–2438 which is entirely incorporated herein by reference.

A growing number of human diseases have been classified as autoimmune or T cell-mediated in nature (see. Theofilopoulos, A., In: D. P. Stites, et al., eds., *Basic and Clinical Immunology*, Lange Medical Publications, Los Altos, Calf. 1988; and Berkow, supra), which references are entirely incorporated by reference; and the present invention is intended to include any and all of such T-cell-mediated diseases in mammals including humans.

As used herein the term "polycyclic aromatic compound" or "hypericin related compound", as described hereins also includes isomers, analogs, derivatives, homologs of polycyclic diones as disclosed in assignee's U.S. patent application Ser. No. 07/413,163, filed Oct. 4, 1989 as a Continuation-in-part of U.S. patent application Ser. No. 07/324,177, filed Mar. 19, 1989 (now abandoned) and PCT application No. PCT/US90/01463 filed Mar. 19, 1990, which applications are herein entirely incorporated by reference.

As used herein the term "major histocompatibility complex" (MHC) refers to the genes and their encoded proteins and glycoproteins which comprise cell surface antigens on virtually all mammalian cells. The MHC molecules play a central role in cell-cell interactions in the mammalian immune system, and are primarily responsible for the rejection of allogeneic tissue or organ grafts. The human MHC is designated HLA and the murine MHC is designated H-2.

Preferred polycyclic aromatic or hypericin related compounds for use in the present invention include hypericin, pseudohypericin or an analog, homolog, derivative, salt or ion pair thereof. Most preferred analogs and derivatives include pseudohypericin, desmethyl hypericin (WIS-3), hypericin diacetate (WIS-6), hypericin hexaacetate, dihydroxydesmethyl hypericin (WIS-7), hypericin methyl ester, hypericin propyl esther, isopropyl desmethyl hypericin, and butyl ester of hypericic acid and mixtures thereof. Preferred salts include sodiums potassium and lithium salts. Preferred ion pairs include hypericin-lysine, hypericin-glutamine, hypericin-ethylenediamine, hypericin TRIS. All polycyclic aromatic compounds are useful in treating T cell-mediated diseases in mammals, however in particular individuals or diseases one polycyclic aromatic compound may be more effective. Identification and selection of the most effective polycyclic aromatic compound for treating a particular T cell-mediated disease can be determined using routine experiments and techniques that are well-known to those of ordinary skill in the art. These techniques include the use of suitable in vivo systems such as those set forth in Examples 1–5 below.

Hypericin (1,3,4,6,8,13-Hexahydroxy-10,11-di-methylphenanthro (1,10,9,8-opqra) perylene-7,14 dione; 4,5,-7, 4',5',7'-hexahydroxy-2,2'-dimethylnapthodianthrone, hypericum red, cyclo-werrol, cycloscan) and related compounds can be provided by any known method steps, including but not limited to chemical synthesis or isolation from natural sources, such as synthesis from emodin (e.g., U.S. Pat. No. 5,120,412 to Mazur et al) or bromoemodin trimethylether (e.g., Brockmann et al, *Naturwiss* 40: 411, 1953 Brockmann et al U.S. Pat. No. 2,707,704; Brockmann et al *Chemische Berichte* 90: 2302, 1957; Brockmann et al *Chemische Berichte* 91: 547, 1958) and isolation from *Hypericum* spp., such as *Hypericum perforatum L; Hypericaceal* (see, e.g., Brockmann et al, *Juotus Liebig's Annalen der Chemie* 53: 1, 1942).

Hypericin and related polycyclic aromatic compounds can also be obtained as described in copending U.S. patent application Ser. No. 07/413,163, filed Oct. 4, 1989 as a continuation-in-part application of U.S. patent application Ser. No. 324,177, filed Mar. 19, 1989 (now abandoned) and corresponding PCT application No. PCT/US90/04163 (filed Mar. 19, 1990), U.S. patent application Ser. No. 07/299,971 and PCT application No. PCT/US90/00398, which applications are herein entirely incorporated by reference.

In one embodiments the method of the present invention comprises treating a mammal having a T cell-mediated disease or symptoms of such a disease by administering an amount of a polycyclic aromatic compound effective to ameliorate or cure the subject of the disease.

"Prevention" involves administration of the composition prior to the induction of the disease. Thus, for example, in an animal model of GVHD, successful administration of composition prior to grafting results in "prevention" of the disease.

"Suppression" involves administration of the composition after the inductive event but prior to the clinical appearance of the disease. Again, in the example of GVHD, successful administration of a composition after injection of the graft cells but prior to the appearance of clinical symptoms comprises "suppression" of the disease.

"Treatment" involves administration of the composition after the appearance of the disease. In the GVHD example, successful administration of a composition after injection of the grafted cells and after clinical signs have developed comprises "treatment" of the disease.

It will be understood that in human medicined it is not always possible to distinguish between "preventing" and "suppressing" since the ultimate inductive event or events may be unknown, latent, or the patient is not ascertained until well after the occurrence of the event or events, thus obscuring the distinction between prevention, suppression or treatment.

Thus, as used herein, the term "treat", "treating" or "treatment" is intended to be inclusive and to mean prophylactic administration to prevent or suppress a disease or, therapeutic administration to treat an active T cell-mediated disease in an afflicted individual.

A subject in need of treatment (including prevention, suppression or treatment, as described above) is one who either is afflicted with the disease, has been subjected to disease-inducing event or events, or for genetic or other reasons is predisposed or susceptible to develop the disease. It will be readily apparent to one of skill in the art in treating T cell-mediated diseases whether a subject is in need of such treatment.

The preclinical and clinical prophylactic and therapeutic use of the present invention in the treatment of T cell-mediated diseases will be best accomplished by those of skill in the relevant arts, employing accepted principles of diagnosis and treatment. Such principles are known in the art, and are set forth, for example, in Braunwald, E. et al., eds., *Harriosn's Principles of Internal Medicine*, 11th Ed., McGraw-Hills publisher, New York, N.Y. (1987), Berkow et al, eds., The Merck Manuals 16th edition, Merck and Co., Rahway, N.J., 1992; Goodman et al., eds., *Goodman and Gilman's The Pharmacological Basis of Therapeutics*, 8th edition, Pergamon Press, Inc., Elmsford, N.Y., (1990); Avery's Drug Treatment: *Principles and Practice of Clinical Pharmacology* and *Therapeutics*, 3rd edition, ADIS Press, LTD., Williams and Wilkins, Baltimore, Md. (1987), Katzung, ed. *Basic and Clinical Pharmacology*, Fifth Edition, Appleton and Lange, Norwalks Conn., (1992), Rakel, ed., *Current Therapy*, W. B. Saunders Co., Philadelphia, Pa. (1992), which references and references cited thereins are entirely incorporated herein by reference.

The preferred subjects for the compositions and methods of the present invention are mammals, preferably humans. Included within the scope of the present invention are all animals which have an immune system and are susceptible to T cell-mediated diseases.

In addition, other experimental systems may be employed to optimize the method of the present invention. For example, the effect of the polycyclic aromatic compounds of the present invention on multiple sclerosis can be examined in the experimental allergic encephalomyelitis (EAE) model in rodents (Higgins et al., supra). EAE is an antigen-induced T cell-mediated autoimmune disease directed against myelin basic protein (MBP). EAE is a recognized and widely used animal model of multiple sclerosis. EAE is induced by parenteral administration of MBP and an adjuvant (such as Freund's complete adjuvant). This treatment induces either a monophasic or an exacerbating/remitting form of demyelinating disease (depending on the species of animal and details of administration) having the characteristics of multiple sclerosis. Such a model is recognized in the art to provide animal in vivo data which is known to correlate with human clinical efficacy.

In like manner, the polycyclic aromatic or hypericin related compounds and compositions of the present invention can be tested by administration to animals afflicted experimental diabetes, using the wellknown spontaneous diabetes models of the BB rat strain or the NOD mouse strain. Alternatively, induced diabetes, for example streptozotocin-induced diabetes in mice, can be used as a model.

The effects of polycyclic aromatic compounds and compositions of the present invention on rheumatoid arthritis may be examined using the mouse model for collagen-induced arthritis (Nagler-Anderson et al., supra), which is known to correlate with human clinical efficacy.

The present invention is also directed to a method for decreasing the lyric activity of cytotoxic T-lympohocytes mostly CD8+ cells and also CD4+ cells expression of CD4 on the surface of T cells. Cytotoxic T cells are incubated in the presence of an effective concentration of a polycyclic aromatic compound according to the present invention for about 1 to 10 minutes. Effective concentrations are from about 0.1 to about 10 µg/ml, preferably about 0.5 to about 5 µg/ml. Target cells, labeled with 51 cromium, against which the CTL cells have previously been sensitized are then added for a period of 2–10 hours. Target cell damage induced by the CTL may be measured by 51 chromium release from the target cells into the growth medium. Inhibition of CTL-mediated target cell lysis is measured as inhibition of 51CY release.

The present invention is also directed to a method for increasing multidrug resistance (mdr) in a cell and enhancing the expression of an mdr protein or glycoprotein, such as MDR-1. Cells are cultured in the presence of various concentrations of a polycyclic aromatic compound such as hypericin or its analogs, derivatives, salts, or ion pairs, as described herein. By continuous culture in the presence of a fixed or increasing concentrations of the compound, for example for a period of several weeks up to several months or even years, the cells are induced to express mdr proteins. This results in a reduction of the net uptake of hypericin, or any of a number of drugs. This phenomenon is known from studies of the expulsion of conventional chemotherapeutic drugs from cells. This mechanism is thought to involve induction of higher levels of expression and/or production of multidrug resistance (mdr) glycoproteins, such as the P-glycoprotein, which act as transporters that pump out antitumor agents (Tsuruo, To et al., *Jpno J. Cancer Res.* (Gann) 79:285–296 (1988), which reference is hereby incorporated by reference in its entirety). Such mdr proteins are well known in the resistance of tumor cells to vinca alkaloid or anthracycline agents, and cells which acquire such resistance generally show cross resistance to other antitumor agents having different structures and different modes of action. Such resistance has also been termed "pleiotropic drug resistance." Multidrug resistant tumor cells show a number of similar cytogenetic and biochemical changes associated with this phenotype.

Cells treated according to the present invention to induce multidrug resistance may be inoculated into an subject, for example, to repopulate the subject with cells having enhanced multidrug resistance.

MRL lpr/lpr mice spontaneously develop an autoimmune lupus-like syndrome, which among other things induces glomerulonephritis which leads to massive proteinuria, kidney destruction and death. MRL lpr/lpr or C3H/lpr mice injected with Hy 2× per week continuously, beginning at three months of age at doses of 50 and 150 microgram per mouse have shown significant reduction in proteinuria (at 50 µg/mouse and prolonged survival in both concentrations).

Polycyclic aromatic compounds of the present invention can also be advantageously combined with one or more of the immunosuppressive agents that are commonly employed to treat mammals afflicted with T cell-mediated diseases. Due to the effectiveness of the polycyclic aromatic compound of the present invention on these diseases, the dosages of the immunosuppressive agents may be lowered such that some or all of the undesired side effects are avoided. Alternative drug regimens can be employed when the immunosuppressive drugs are administered in combination with the polycyclic aromatic compounds of the present invention, for example, alternating doses of the compounds of the present invention and the immunosuppressive drugs, thereby reducing the frequency of administration and toxic side effects of these agents. Non-limiting examples of the immunosuppressive agents that can be used in above combinations include cyclosporin A (Sandoz Pharmaceuticals, East Hanover, N.J.), Imuran (azathioprine, Burroughs Welcome, Research Triangle Park, N.C.), Cytoxan, (cyclophosphamide, Bristol Meyers Oncology, Evansville, Ind.), prednisone (Lederle Laboratories, Wayne, N.J.), methylprednisolone (Duramed Pharmaceuticals, Cincinnati, OH) and OKT-3 monoclonal antibodies (Ortho Diagnostics, Raritan, N.J.), FK-506 (which can be obtained from the fermentation broth of *Streptomyces tsukubaensis* and is available from Fujisawa Pharmaceutical Co., Osaka, Japan) (Thomas, J, et al., *Transplantation* 49:390–396, 1990).

Effective treatment of a given T cell-mediated disease may be achieved by using a single one of such polycyclic aromatic compounds, or a combination of two or more of such compounds. That is to say, two or more polycyclic aromatic compounds may be administered simultaneously or sequentially. Naturally, it is desirable to employ the lowest effective dose of the polycyclic aromatic compound (compounds) and/or immunosuppressive agents of the present invention that will provide a significant beneficial effect to the patient. What constitutes "significant effect" varies among patients as well as among the various diseases. Moreover, the polycyclic aromatic compound or mixtures thereof may constitute the sole active ingredient of the composition of the present invention or the polycyclic aromatic compound may be administered in conjunction with other agents or ingredients (such as immunosuppressive agents as disclosed herein) as part of a single composition for treating the disease or otherwise ameliorating or abolishing the T cell-mediated disease or the symptoms of such a disease.

A preferred embodiment is a method for treating or preventing a T cell-mediated disease by administering to a mammal in need of such treatment an amount of (a) a polycyclic aromatic or hypericin related compound and (b) an immunosuppressive agent, the combined amount of (a) and (b) in combination being effective to treat or prevent the T cell-mediated disease, Determination of the most effective compound or mixture of compounds for a use in treating a mammal afflicted or at risk for the particular T cell-mediated disease can be accomplished by routine experimentation using suitable and well known experimental models as described above.

When employed to treat a T cell-mediated diseased the pharmaceutical formulations of the present invention may be administered preferably orally, topically or preferably parenterally, and most preferably intravenously at dosages which can be broadly defined by reference to hypericin as follows below. The preference is orally for diseases like lupus and rhematoid arthritis and intravenously for graft versus host disease during bone marrow transplantation and tissue graft rejection, and topically or orally for skin diseases such as dermatomyositis, scleroderma.

The present invention also provides compositions or pharmaceutical formulations or dosage forms for treating or preventing a T cell-mediated disease. Compositions or pharmaceutical formulations comprising the polycyclic aromatic compound of the present invention as the sole, active ingredients can be used at dosages (based on hypericin) containing from about 0,001 µg/kg to about 10 mg/kg body weight per treatment, preferably between about 2 µg/kg and about 2 mg/kg body weight per treatment, and most preferably between about 0.1 mg/kg and about and 1 mg/kg body weight per treatment. The frequency of administration can vary from daily, twice daily, 2-, 3-, 4- or 5-times a week depending upon the patient's condition, response to the treatment and the severity of the patient's disease.

When one or more polycyclic aromatic compound is used as the active ingredient, the broad dosages will generally be the same as with hypericin. Moreover, when more than one active ingredient is used in a therapeutic or prophylactic regimen according to the invention (i.e., at least one non-polycyclic aromatic dione compound agent is included), the minimum dosage of the polycyclic aromatic dione compound component (i.e., the polycyclic aromatic compound or compounds) of this regimen may be reduced.

Finally, when more than one active ingredient is used and there is synergism between the polycyclic aromatic dione compound component and the other ingredient or ingredients (or between two or more polycyclic aromatic compound compounds, even in single active ingredient regimens, i.e., in regimens where the only agent or agents used are polycyclic aromatic diones or hypericin related compounds), the minimum effective polycyclic aromatic or hypericin related compound dosages will be even lower. It should be also understood that analogous minimum dosage modifications apply when a stabilizing or potentiating agent is used in conjunction with a polycyclic aromatic compound, or when a slow release form of a prodrug is used, such as hypericin hexaacetate, which will require esterases to hydrolyse the acetates and convert it to hypericin, is used.

When one or more immunosuppressive agent is used in combination with the compounds of the present invention, the agent may be administered in conjunction with at least one polycyclic aromatic or hypericin related compound at doses dependent on the individual agent used. "In conjunction" is defined herein to mean contemporaneous administration or sequential administration. The polycyclic aromatic or hypericin related compound may be administered first and the immunosuppressive agent later, or vice versa.

For example, when cyclosporin A is used in conjunction with the polycyclic aromatic compound of the present invention, the cyclosporin may be administered to a subject at dosages broadly ranging between about 0.01 and about 100, such as 0.02, 0.04, 0.06, 0.08, 0.1, 0.2, 0.3, 0.4, 0.5, 0.6, 0.7, 0.8, 0.9, 1.0, 1.9, 2.0, 2.9, 3, 5, 9, 10, 20, 30, 40, 50, 60, 70, 80, 90 or mg/kg body weight per day or any range therein. This may be less (in certain instances) than the normal cyclosporin dose which is between about 1 and 20 mg/kg body weight per day for treating kidney graft rejection in humans. In like manner, azathioprine (Imuran™) can be used at dosages broadly ranging between about 0.1 and 20 mg/kg body weight per day, while prednisone may be administered at dosages broadly ranging between about 0.1 mg and 200 mg/kg body weight per day. The amounts of these agents used can be determined and optimized using routine experimentation well-known in the art as described above.

The duration and number of doses or treatments required to control the disease will vary from subject to subject, depending upon the severity and stage of the illness and the subject's general condition and will also depend on the specific activity of each polycyclic aromatic compound and/or immunosuppressive agent as well as their toxicity (if any). The total dose required for each treatment may be administered in divided doses or in a single dose. The treatment may be administered daily, one to ten times daily, or two to five times a week, or as determined by the subject,s condition and the stage of the disease. The treatments may be initiated befores substantially simultaneously with or after the onset of a T cell-mediated disease as defined herein. For example, when treating a mammal who will undergo a tissue transplantation, the pharmaceutical formulations of the present invention may be administered 1–15 days before the transplantation as well as 1–360 days after the transplantations or at any time after transplantation when signs at graft rejection are detected.

A polycyclic aromatic or hypericin related compound of the present invention can be incorporated in conventional, solid and liquid pharmaceutical formulations (e.g. tablets, capsules, caplets, injectable and orally administrable solutions) or locally by using suppositories for use in treating mammals that are afflicted with T cell-mediated diseases. Topically by incorporation into skin penetrating creams or propylene-glycol, or other creams which are absorbed into the deep layers of the skin. The pharmaceutical formulations of the invention comprise an effective amount of the polycyclic aromatic compound of the present invention as one of the active ingredients in combination with an immunosuppressive agent as discussed above. For example, a parenteral therapeutic pharmaceutical formulation may comprise a sterile isotonic saline solution containing between about 0.001 micrograms and about 100,000 micrograms of the polycyclic aromatic compounds of the present invention and between about 0.01 mg per kg and 100 mg of the immunosuppressive agent as described above. It will be appreciated that the unit content of active ingredients contained in an individual dose of each dosage form need not in itself constitute an effective amount since the necessary effective amount can be reached by administration of a plurality of capsules, tablets, injections or combinations thereof.

Pharmaceutical formulations of the present invention may contain well known inert constituents including pharmaceutically-acceptable carriers, diluents, fillers, salts, and other materials well known in the art, the selection of which depends upon the dosage form utilized and the particular purpose to be achieved according to the determination of the ordinarily skilled artisan in the field. For example, tablets may be formulated in accordance with conventional procedures employing solid carriers well known in the art. Examples of solid carriers include carboxymethyl cellulose, starch, sugar, bentonite, silica and other commonly used carriers and enteric coatings. Aqueous solutions of propylene glycol, polyethylene glycol, benzyl alcohol, isopropanol, ethanol, dimethylsulfoxide (DMSO), dimethylacetamide or other biologically acceptable organic solvents and aqueous detergent solutions, such as 1–5% Tween 80, or aqueous solutions may be employed. Mixtures of aqueous solutions (e.g. water with a pH higher than 7 and preferably about 8 or 5% dextrose) with basic amino acids such as lysine or aqueous solutions containing Tris buffer and/or, 2–2.5% benzyl alcohol may be used as diluents, carriers or solvents in the preparation of solid and liquid pharmaceutical formulations containing the compositions of the present invention. Further non-limiting examples of carriers and diluents include carbohydrates, cyclodextrans, albumin and/or other plasma protein components such as low density lipoproteins, high density lipoproteins and the lipids with which these serum proteins are associated. Such lipids include phosphatidyl choline, phosphatidyl serine, phosphatidyl ethanolamine and neutral lipids such as triglycerides. Lipid carriers also include, without limitation, tocopherol and retinoic acid. Conventional liposomes, well known in the art, containing the formulations of the present invention may also be employed as a drug delivery system. Semisolid shaped formulations such as those well-known in the art (e.g. suppositories) are also contemplated for use in administering the active ingredients of the present invention or creams containing Hy or analogs thereof for topical administration.

The carrier for the active ingredient may be either in sprayable or nonsprayable form. Non-sprayable forms can be semi-solid or solid forms comprising a carrier conducive to topical application and having a dynamic viscosity preferably greater than that of water. Suitable formulations included but are not limited to, solution, suspensions, emulsions, creams, ointments, powders, liniments, salves, and the like. If desired, these may be sterilized or mixed with auxiliary agents, e.g., preservatives, stabilizers, wetting agents, buffers, or salts for influencing osmotic pressure and the like. Preferred vehicles for non-sprayable topical preparations include ointment bases, e.g. polyethylene glycol-1000 (PEG-1000), conventional creams such as HEB cream; gels; as well as petroleum jelly and the like.

Suitable formulations for topical administration include creams, gels, jellies, mucilages, pastes and ointments. The compounds may also be formulated for transdermal administration, for example, in the form of transdermal patches so as to achieve systemic administration.

Also suitable for systemic or topical application, in particular to the mucus membranes and lungs, are sprayable aerosol preparations wherein the active ingredient, preferably in combination with a solid or liquid inert carrier material. The aerosol preparations can contain solvents, buffers, surfactants, perfumes, and/or antioxidants in addition to the proteins or peptides of the present invention. For aerosol administration, the therapeutic agents in accordance with the present invention may be packaged in a squeeze bottle, or in a pressurized container with an appropriate system of valves and actuators. Preferably, metered valves are used with the valve chamber being recharged between actuation or dose, all as is well known in the art.

Preferred parenteral dosage forms may comprise an aqueous solution comprising 2% benzyl alcohols further diluted in 5% dextrose to a volume of 50 to 500 ml, containing between about 0.05 μg and about 1 gram of the polycyclic aromatic compounds of the present invention and between about 0.01 mg and 1000 mg of an immunosuppressive agent. Capsules employed in the present invention may be made from any pharmaceutically acceptable material, such as gelatin or cellulose derivatives. Sustained release oral and transdermal delivery systems may also be employed to administer the active ingredients of the present invention.

Having now generally described the invention, the same will be more readily understood through reference to the following examples which are provided by way of illustrations and are not intended to be limiting of the present invention, unless specified.

EXAMPLE I

The Effect of Hypericin on Graft-versus-Host Disease

GVHD in mice is a well recognized model of a T cell-mediated disease. C3H/DiSN mice which have the MHC type $H-2^k$ and BALB/c mice which are $H-2^k$ were obtained from The Jackson Labs, Bar Harbor, Me.). These strains were crossed to produce (C3H×BALB/c) $F_1$ offspring ($H-2^k/H-2^d$), which were irradiated with a sublethal dose (450 rad) of ionizing radiation from a Cs-137 source providing radiation at 390 rads/minute, for 1.2 minutes. Irradiated mice were reconstituted by intravenous injection of either $5\times10^6$ or $2\times10^7$ immunocompetent cells derived from the spleen and bone marrow of C3H mice, as described in Rappaport, H. et al., *Amer. J. Pathol.* 96:121–142, 1979. In this system, the host cannot recognize the transferred C3H cells and cannot reject them. However, the grafted immunocompetent cells recognize the class I and class II $H-2^d$ antigens on the host's cells as foreign and elicit a cell-mediated immune response across these class I and class II major histocompatibility barrier. This reaction involves an initial large expansion of donor T cells followed by the generation of donor derived T effector cells, including cytotoxic T lymphocytes (CTL) capable of attacking and destroying host tissues. This process also involves increased production and secretion of lymphokines and monokines, including IL-1, which causes fever and malaise and contributes to the production and TNFβ. TNFα and IL-2, the latter of which promotes lymphocyte proliferation. These substances contribute to the processes of weight loss and runting known as cachexia which progressively exacerbate vascular leakage and the sickness of the animals, leading to ruffled fur and death of 100% of the mice within 20–40 days.

The grafted mice were injected with hypericin intraperitoneally at doses of 10, 50 and 150 μg/mouse administered 3 times a week (every other day) beginning on day 8 after irradiation and cell inoculation. The results of this experiment are shown in FIG. 1. At the cell inoculum useds 2 mice in the hypericin-treated group (one receiving 10 μg and one receiving 150 μg micrograms of hypericin) remained alive. Hypericin injections were discontinued 50 days after cell transfer and the surviving mice remained alive 21 additional days.

Figure 2:
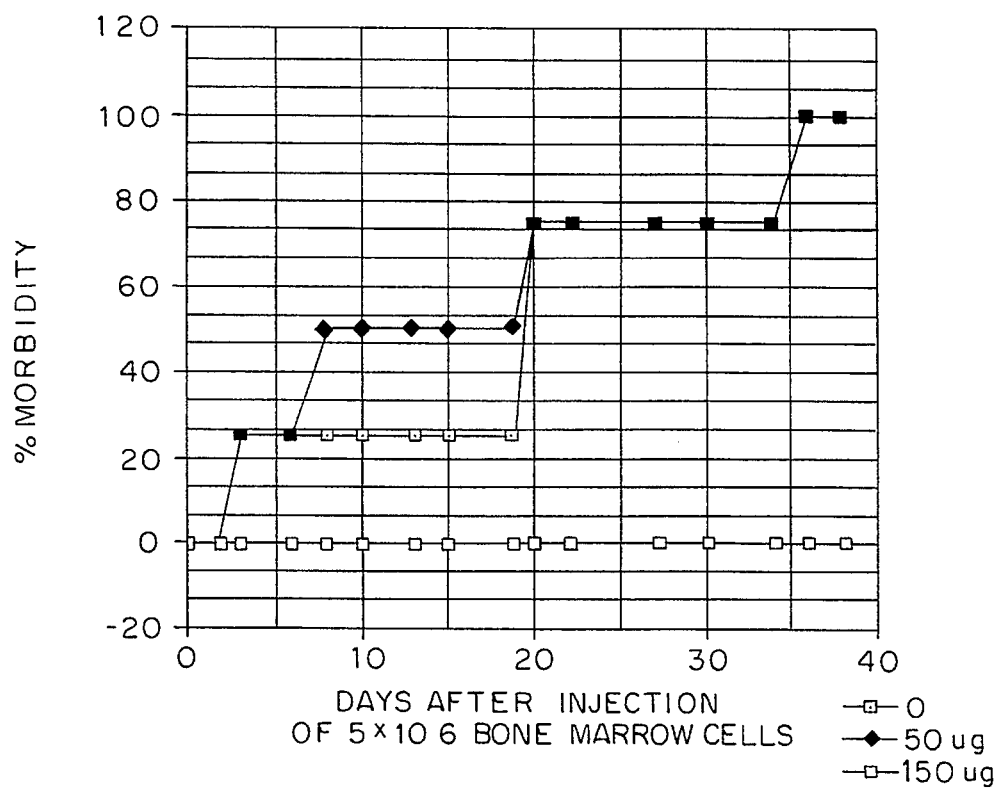
FIG. 2 is a graph showing the effect of hypericin on GVHD morbidity in mice treated 3 times a week with hypericin.

In a second experiment recipient mice were treated as above, inoculated with $2\times10^7$ or $5\times10^6$ cells and followed for 40 days post-transplantation. The results of these inoculations are depicted in FIG. 2 and set forth quantitatively in Table 1.

In the data presented below in Table I is the morbidity observed in the inoculated mice was scored as follows:

| | |
|---|---|
| 0 | mouse healthy, active and escapes attempts at physical contact; fur smooth; |
| + | mouse appears sick, movements slow; fur rough; |
| 2+ | pronounced lethargy, mouse tends to remain motionless and does not attempt to escape from capture; |
| 3+ | mouse assumes hump back shape, confines itself to the corners of the cage without movement; weight loss evident; fur ruffled; |
| 4+ | pronounced weight loss and cachexia; fur very ruffled; shivering is obvious; and |
| D. | death |

TABLE I

| Number of Cells Inoculated | Treatment | Morbidity (days post-transplantation) | | | | | | | | | | | | | | | | |
|---|---|---|---|---|---|---|---|---|---|---|---|---|---|---|---|---|---|---|
| | | 12 | 15 | 16 | 19 | 21 | 23 | 26 | 28 | 32 | 33 | 35 | 40 | 43 | 47 | 49 | 51 | 54 | 55 |
| 0 | None (no irradiation, no cells) | 0 | 0 | 0 | 0 | 0 | 0 | 0 | 0 | 0 | 0 | 0 | 0 | 0 | 0 | 0 | 0 | 0 | 0 |
| | | 0 | 0 | 0 | 0 | 0 | 0 | 0 | 0 | 0 | 0 | 0 | 0 | 0 | 0 | 0 | 0 | 0 | 0 |
| 0 | None (no irradition, no cells) | 0 | 0 | 0 | 0 | 0 | 0 | 0 | 0 | 0 | 0 | 0 | 0 | 0 | 0 | 0 | 0 | 0 | 0 |
| | | 0 | 0 | 0 | 0 | 0 | 0 | 0 | 0 | 0 | 0 | 0 | 0 | 0 | 0 | 0 | 0 | 0 | 0 |
| | | 0 | 0 | 0 | 0 | 0 | 0 | 0 | 0 | 0 | 0 | 0 | 0 | 0 | 0 | 0 | 0 | 0 | 0 |
| $5 \times 10^6$ | None | 0 | 0 | 0 | 0 | 0 | 0 | 0 | 0 | 0 | + | + | + | +2 | +2 | +3 | +3 | +3 | +3 |
| | | 0 | 0 | + | + | + | + | + | +3 | +3 | +4 | D | D | D | D | D | D | D | D |
| | | 0 | 0 | 0 | 0 | 0 | 0 | 0 | 0 | 0 | + | +2 | + | + | + | +2 | +2 | +2 | +2 |
| | | 0 | 0 | 0 | 0 | 0 | 0 | 0 | 0 | 0 | 0 | + | 0 | 0 | 0 | + | + | + | + |
| $5 \times 10^6$ | 50 micrograms Hypericin | 0 | 0 | + | + | +2 | +3 | +3 | +3 | +3 | +3 | +3 | +3 | +3 | +3 | +3 | +3 | +3 | +3 |
| | | 0 | 0 | 0 | 0 | 0 | 0 | 0 | 0 | 0 | + | + | + | + | + | + | + | + | + |
| | | 0 | 0 | 0 | 0 | + | + | D | D | D | D | D | D | D | D | D | D | D | D |
| | | 0 | 0 | 0 | 0 | 0 | 0 | 0 | 0 | 0 | 0 | 0 | 0 | 0 | 0 | 0 | 0 | 0 | + |
| $5 \times 10^6$ | 150 micrograms Hypericin | 0 | 0 | 0 | 0 | 0 | 0 | 0 | 0 | 0 | 0 | 0 | 0 | 0 | 0 | 0 | 0 | 0 | 0 |
| | | 0 | 0 | 0 | 0 | 0 | 0 | 0 | 0 | 0 | 0 | 0 | 0 | 0 | 0 | 0 | 0 | 0 | 0 |
| | | 0 | 0 | 0 | 0 | 0 | 0 | 0 | 0 | 0 | 0 | 0 | 0 | 0 | 0 | 0 | 0 | 0 | 0 |
| | | 0 | 0 | 0 | 0 | 0 | 0 | 0 | 0 | 0 | 0 | 0 | 0 | 0 | 0 | 0 | 0 | 0 | 0 |
| $2 \times 10^7$ | None | 0 | + | + | + | D | D | D | D | D | D | D | D | D | D | D | D | D | D |
| | | + | +2 | +2 | D | D | D | D | D | D | D | D | D | D | D | D | D | D | D |
| | | 0 | + | + | + | + | + | + | +2 | +2 | +2 | +2 | D | D | D | D | D | D | D |
| | | 0 | 0 | 0 | 0 | + | + | + | + | + | + | + | +2 | +2 | +2 | +2 | +2 | +2 | +2 |
| $2 \times 10^7$ | 50 micrograms Hypericin | — | — | — | — | — | — | — | — | — | — | — | — | — | — | — | — | — | — |
| | | 0 | 0 | 0 | + | + | + | + | +2 | +2 | +3 | +4 | — | — | — | — | — | — | — |
| | | 0 | 0 | + | + | +2 | +2 | +2 | +3 | +3 | +4 | +4 | +4 | +4 | — | — | — | — | — |
| | | + | +3 | +4 | D | D | D | D | D | D | D | D | D | D | D | D | D | D | D |
| $2 \times 10^7$ | 150 micrograms Hypericin | +2 | — | D | D | D | D | D | D | D | D | D | D | D | D | D | D | D | D |
| | | 0 | 0 | + | +3 | — | D | D | D | D | D | D | D | D | D | D | D | D | D |
| | | + | +2 | +3 | +3 | +3 | +3 | +4 | +4 | +4 | D | D | D | D | D | D | D | D | D |
| | | 0 | 0 | + | +3 | — | D | D | D | D | D | D | D | D | D | D | D | D | D |

Table 1 and FIG. 2 show the results of morbidity and survival. At a cell inoculum of 5×10⁶ cells/mouse, all of the control mice began manifesting symptoms of GVHD as early as day 16 after transplantation and by day 35, all of the control mice were affected (Table 1). One of four mice which received 50 μg hypericin three times a weeks was symptom-free until day 55 after-inoculation. Howevers all of the mice that received 150 μg hypericin remained healthy throughout the entire experiment. When a large inoculum of grafted cells was used to induce GVHD (2×10⁷ cells), hypericin was not effective at 150 μg/mouse.

These results establish that hypericin was effective in lessening the symptoms of GVHD and prolonging the survival of treated animals.

EXAMPLE II

Effect of Different Frequencies of Hypericin Administration on Acute GVHD

The same mouse strain combination was used as above. C3H spleen and bone marrow cells (10⁷) were injected into irradiated (C3H×BALB/c) F₁ hybrids. Eight days laters hypericin at 150 μg/mouse was injected traperitoneally (in 0.5 ml H₂O) into the mice 0, 1, 2, 3, 4 or 5 times/week continuously up to day 70. The mice were then followed for survival over a 70 day follow-up period.

Figure 3A:
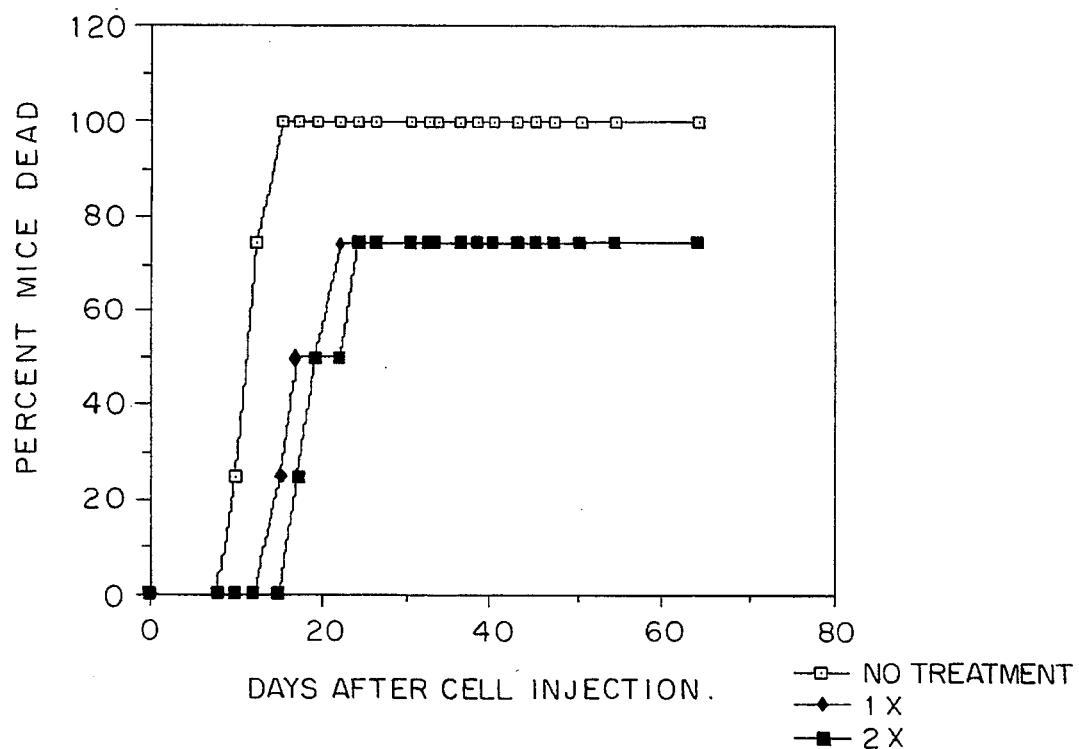
FIG. 3A and 3B are graphs showing a comparison of the efficacy of one, two, three, four or five weekly administrations of hypericin in the treatment of GVHD in mice.
Figure 3B:
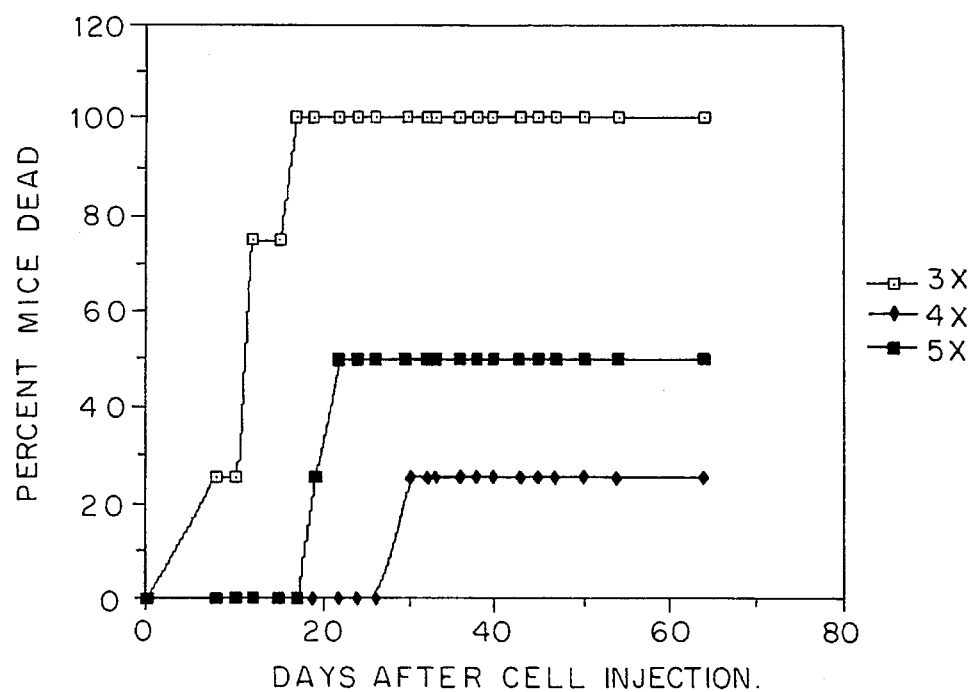

As is shown in FIGS. 3A and 3B, only 1 of 4 mice injected with hypericin 4 times/week died, and 2 of 4 mice died in the group injected 5 times/week. In this groups death occurred 15–20 days later than in the control group. In the no hypericin control group and in the group injected with hypericin only 3 times/weeks all the mice died.

These results show that hypericin treatment, at a frequency of four and five times per week was more effective in treating GVHD than a three injections per week regimen.

EXAMPLE III

Effects of Hypericin Analogs and Derivatives on GVHD

The effect of three hypericin analogs and derivatives, hypericin diacetate (WIS-6), desmethyl hypericin (WIS-3) and dihydroxydesmethyl hypericin (WIS-7) were tested in the GVHD system. These treatments were compared with hypericin or cyclosporin A (Sandoz Pharmaceuticals, East Hanover, N.J.), one of the most effective treatments currently used to suppress T cell-mediated diseases. The experiments were conducted as described in Examples I and II, above. Each of the drugs was injected intraperitoneally in 0.5% ethanol at a dosage of 150 μg/mouse, three times/week. The results of this experiment are shown in FIG. 4 and Table 2.

mice remained healthy until day 32 but rapidly became sick thereafter, perhaps due to the toxicity of WIS-3 at that dosage.

Figure 4A:
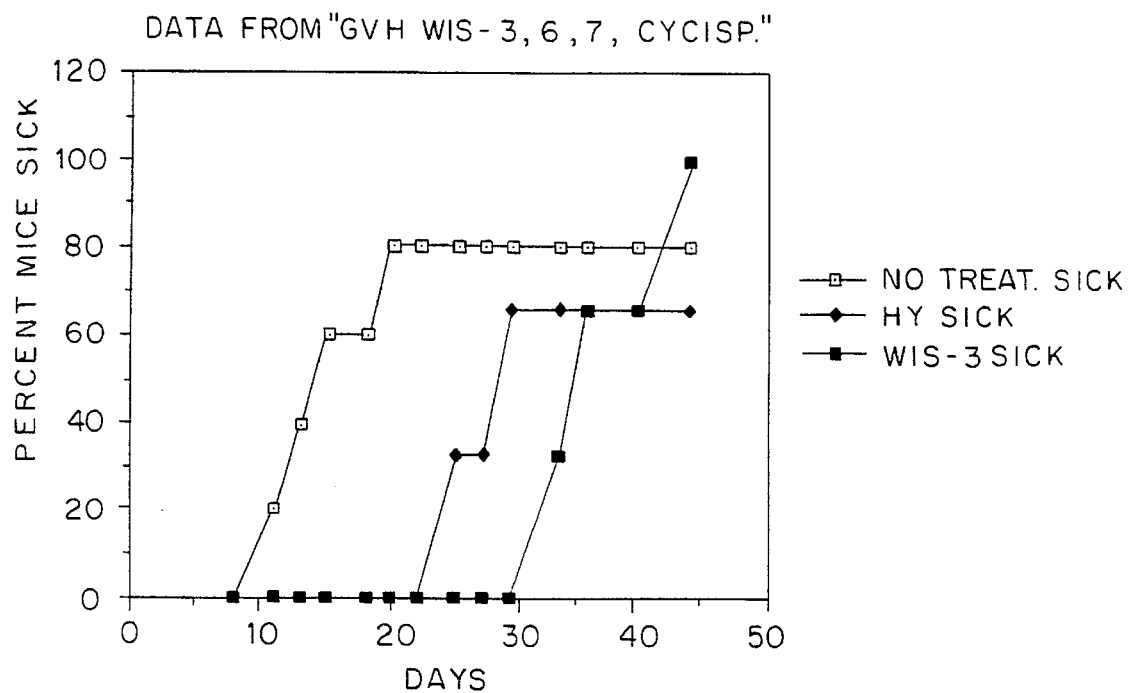
FIG. 4A and 4B are graphs showing the effects of cyclosporin A, hypericin and the hypericin analogs WIS-3, WIS-6 and WIS-7 on morbidity of mice with GVHD.
Figure 4B:
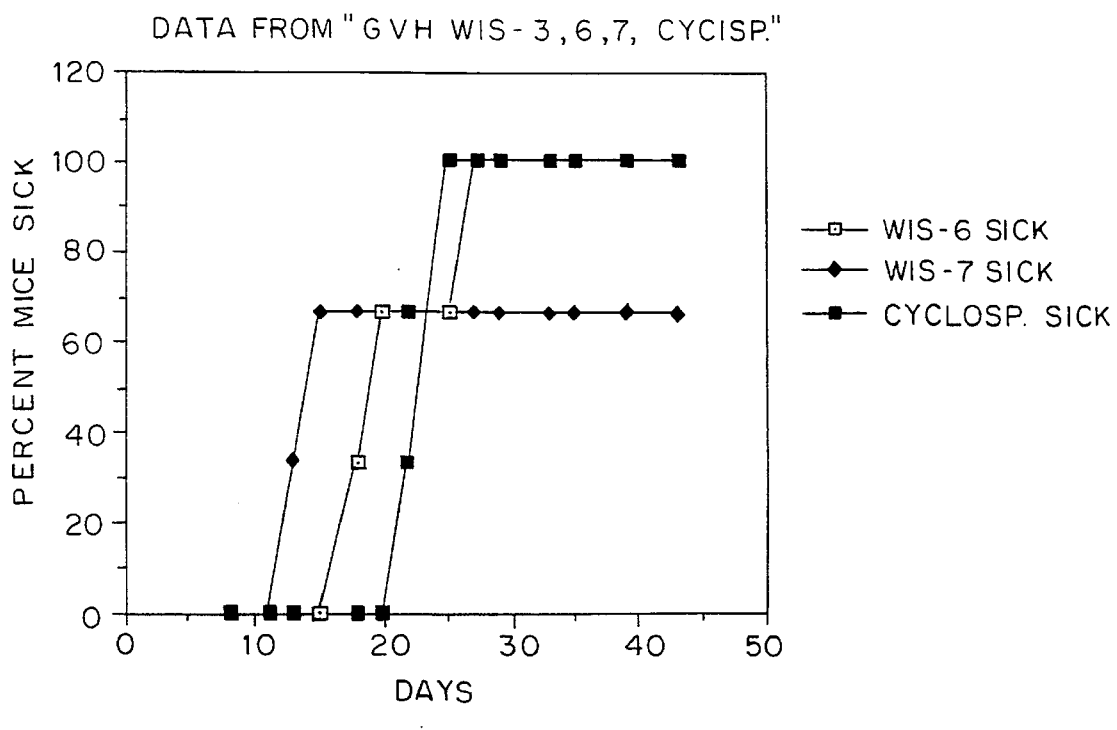

FIG. 4B shows that only 60% of the animals treated with WIS-7 were sick by day 46 post-transplantation compared to 100% of mice treated with WIS-6 or cyclosporin A.

Figure 5A:
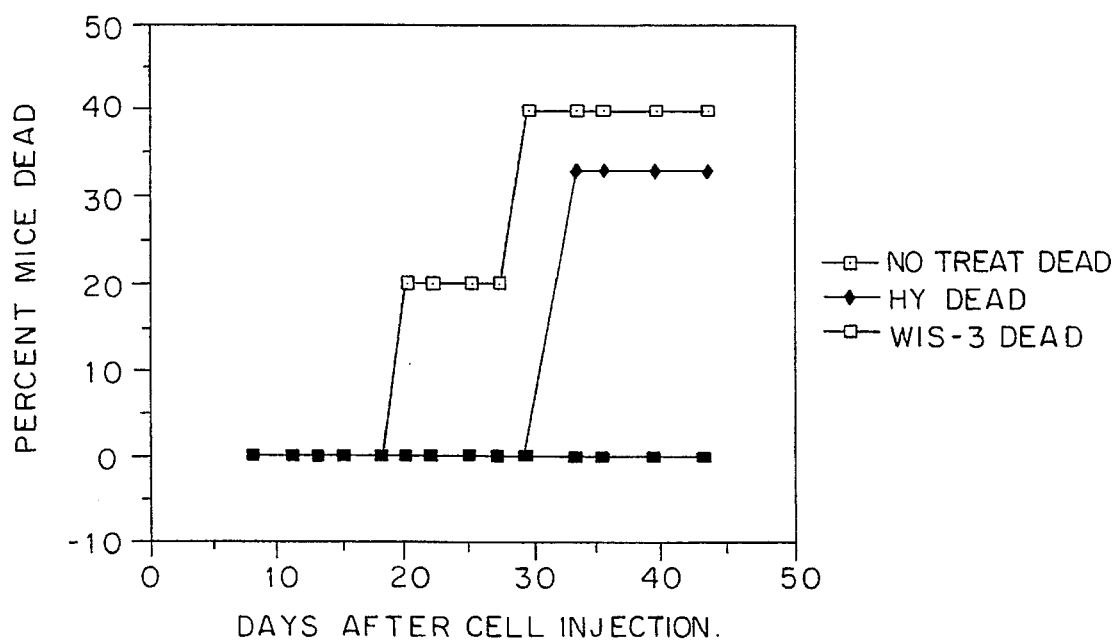
FIG. 5A and 5B are graphs showing the effects of cyclosporin A, hypericin and the hypericin analogs WIS-3 (desmethyl-hpericin), WIS-6 (hypericin diacetate) and WIS-7 (dihydroxy desmethyl hypericin) on survival of mice with GVHD.
Figure 5B:
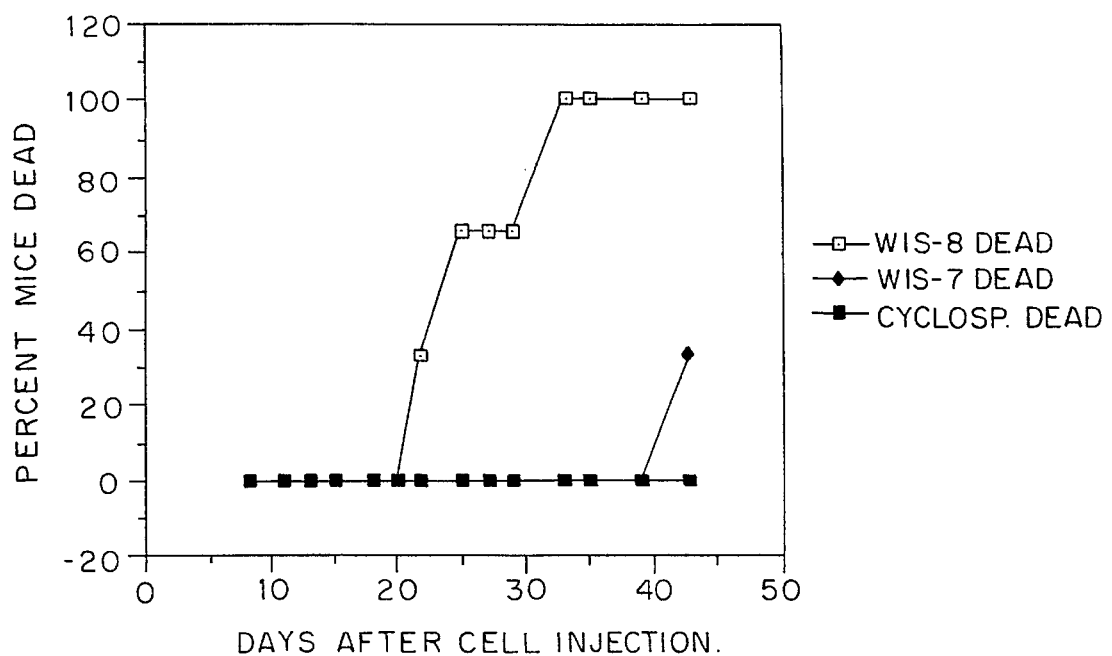

FIG. 5A and 5B shows the survival of mice treated as described above. As is seen in FIG. 5A, 40% of the control mice (irradiation and transplanted cells) were dead by day 46 as compared to only 33% of the hypericin-treated mice and 0% of the WIS-3 (desmethyl hypericin)-treated mice. Time of death of the hypericin-treated mice was delayed from day 17 (controls) to day 30. FIG. 5B shows that 0% of mice which received cyclosporin A were dead by day 46 whereas 100% of mice receiving WIS-7 and 33% of the mice which received WIS-7 were dead by day 46.

These results show that hypericin, WIS-7 (and perhaps WIS-3) were more effective in treating GVHD than was cyclosporin A.

TABLE II

| Number of Cells Inoculated | Treatment | Morbidity (days post-transplantation) | | | | | | | | | | | | |
|---|---|---|---|---|---|---|---|---|---|---|---|---|---|---|
| | | 0 | 11 | 15 | 18 | 21 | 22 | 25 | 28 | 32 | 36 | 39 | 41 | 46 |
| 0 | None (no irradiation, no cells) | 0 | 0 | 0 | 0 | 0 | 0 | 0 | 0 | 0 | 0 | 0 | 0 | 0 |
| | | 0 | 0 | 0 | 0 | 0 | 0 | 0 | 0 | 0 | 0 | 0 | 0 | 0 |
| | | 0 | 0 | 0 | 0 | 0 | 0 | 0 | 0 | 0 | 0 | 0 | 0 | 0 |
| 0 | None (no irradiation only) | 0 | 0 | 0 | 0 | 0 | 0 | 0 | 0 | 0 | 0 | 0 | 0 | 0 |
| | | 0 | 0 | 0 | 0 | 0 | 0 | 0 | 0 | 0 | 0 | 0 | 0 | 0 |
| $1 \times 10^7$ | None | 0 | 0 | 0 | 0 | + | +2 | +3 | D | D | D | D | D | D |
| | | 0 | 0 | + | + | +2 | +3 | +3 | +3 | +3 | +3 | +3 | +3 | D |
| | | 0 | 0 | + | D | D | D | D | D | D | D | D | D | D |
| | | 0 | 0 | 0 | + | +3 | D | D | D | D | D | D | D | D |
| $1 \times 10^7$ | 150 micrograms WIS-6 | 0 | 0 | 0 | 0 | + | + | D | D | D | D | D | D | D |
| | | 0 | 0 | + | D | D | D | D | D | D | D | D | D | D |
| | | 0 | 0 | 0 | 0 | + | + | +2 | D | D | D | D | D | D |
| | | 0 | 0 | 0 | 0 | +2 | D | D | D | D | D | D | D | D |
| $1 \times 10^7$ | 150 micrograms WIS-3 | 0 | 0 | 0 | 0 | + | +2 | D | D | D | D | D | D | D |
| | | 0 | + | + | D | D | D | D | D | D | D | D | D | D |
| | | 0 | 0 | 0 | + | + | +2 | D | D | D | D | D | D | D |
| | | 0 | 0 | 0 | 0 | + | +2 | D | D | D | D | D | D | D |
| $1 \times 10^7$ | 150 micrograms hypericin | 0 | 0 | 0 | 0 | 0 | 0 | 0 | 0 | 0 | 0 | 0 | 0 | 0 |
| | | 0 | 0 | 0 | 0 | 0 | 0 | 0 | 0 | 0 | 0 | 0 | 0 | 0 |
| | | 0 | 0 | 0 | + | D | D | D | D | D | D | D | D | D |

As is shown in Table 2, mice in the control groups (irradiation and cells only) began manifesting symptoms of GVHD as early as 15 days post-transplantation. Three of four were dead by day 28. WIS-3 and WIS-6 may have had a small effect in ameliorating GVHD symptoms. In contrast, 2 of 3 hypericin-treated mice were healthy and showed no symptoms of GVHD throughout the entire 46 day follow-up period.

The results depicted in FIG. 4 A and B show that treatment with WIS-3 (desmethyl hypericin) appears superior to treatment with cyclosporin A. Both hypericin diacetate (WIS-6) and dihydroxydesmethyl hypericin (WIS-7) appeared to have a small effect in preventing or ameliorating GVHD, compared to the no drug group.

FIG. 4A indicates that 80% of the untreated mice were sick by day 46. Hypericin treatment lowered the number of sick mice to 60% and delayed the appearance of symptoms from day 8 (in the untreated group) to day 22. WIS-3-treated

EXAMPLE IV

Effects of Hypericin and Related Polycyclic Aromatic Compounds on Autoimmune Disease (EAE).

Guinea pig myelin basic protein (GP-MBP), obtained from guinea pig brain tissue (Pel Freeze Rogers, Arkansas) is purified by the method of Diebler, G.E. et al., *Anal. Biochem.* 2:139, 1972). Lewis rats, age 6–8 weeks (Charles Rivers Wilmington, Mass.) is inoculated on day 0 with 10 μg GP-MBP in their foot pads in Freund's complete adjuvant (Difco, Detroit, Mich.) as disclosed in Higgins et al., (supra). The rats are treated with various doses of hypericin, WIS-3, WIS-6 or WIS-7 three and five times a week and monitored for symptoms of EAE.

Immunization of the rats to induce EAE on day 0 is expected to result in an acute paralytic disease with symptoms appearing on day 12 to 14 post-immunization. The rats are scored using the following system: 0=normal; 1=loss of tail tone, 2=weakness of back legs; 3=paralysis of back legs; 4=front leg weakness; 5=moribund.

An additional set of animals are pretreated with various doses of hypericin, WIS-3, WIS-6 or WIS-7 beginning 7–10 days before the induction of EAE on day 0 to determine the effects of these polycyclic aromatic compound on disease induction.

It is anticipated that polycyclic aromatic compound of the present invention will be effective in both preventing the induction of EAE and ameliorating its symptoms.

EXAMPLE V

Effects of Hypericin and Related Polycyclic Aromatic Compounds on Autoimune and Lymphoproliferative Disease in MRL Mice MRL(lpr/lpr) mice spontaneously develop and autoimmune and lymphoproliferative disease characterized by lymphadenopathy, and autoimmune glomerulonephritis, leading to death. The symptoms and the immune complexes which affect the kidneys are similar to those exhibited by humans suffering from systemic lupus erythematosus. The MRL (lpr/lpr) or other mice strains into which the lpr glue has been incorporated such as the C3H/lpr/lpr thus, considered to be a - - - model for SLE. Typically, disease symptoms develop over time beginning as early as 4–6 weeks and continuing over several months, until animals begin to die.

Figure 6:
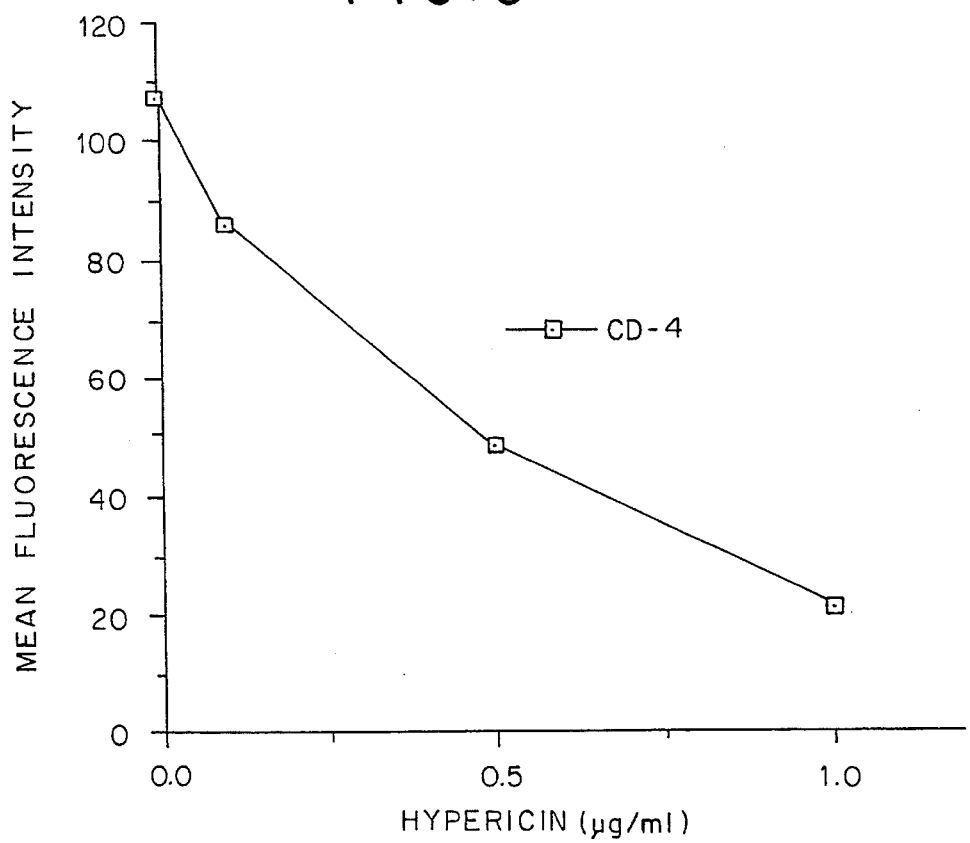
FIG. 6 is a graph showing that hypericin causes a dose-dependent inhibition of CD4 expression on the surface of human T cells of the Supt-1 line.

In the present study, groups of C3H(lpr/lpr) mice were treated with various doses of hypericin (0, 10, 50 or 150 µg/mouse) twice weekly beginning at about weeks and continuing for 4 months. Mortality was scored, and kidneys were removed for later analysis. The results appear in FIG. 6.

Treatment with 10 or 50 µg hypericin resulted in a dramatic increase in survival 120 days after initiation of treatment. Compared to controls, 150 µg of hypericin also lead to a more modest, yet also significant, enhancement of long term survival. Examination of protein secretion in urine (proteinuria) has revealed that mice injected with hypericin, particularly at a dose of 50 µg/mouse exhibited dramatically less proteinuria indicating that kidneys show significantly less of glomerulonephritis in surviving mice treated with hypericin.

Figure 10:
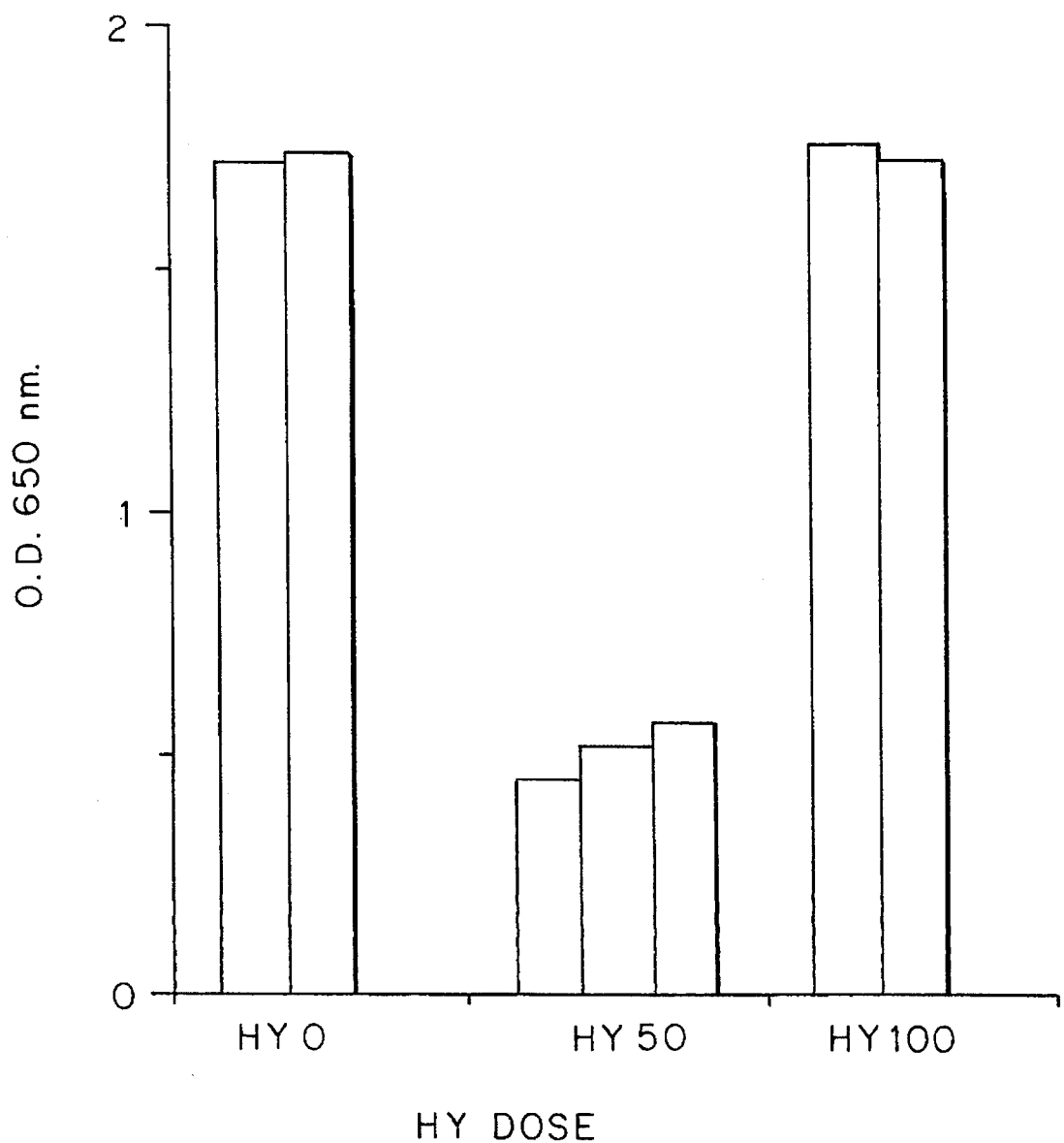
FIG. 10 is a graphical respresentation showing the effect of 3x/week intraperitoneal injections of HY on proteinuria of C3H/lpr mice.
Figure 11:
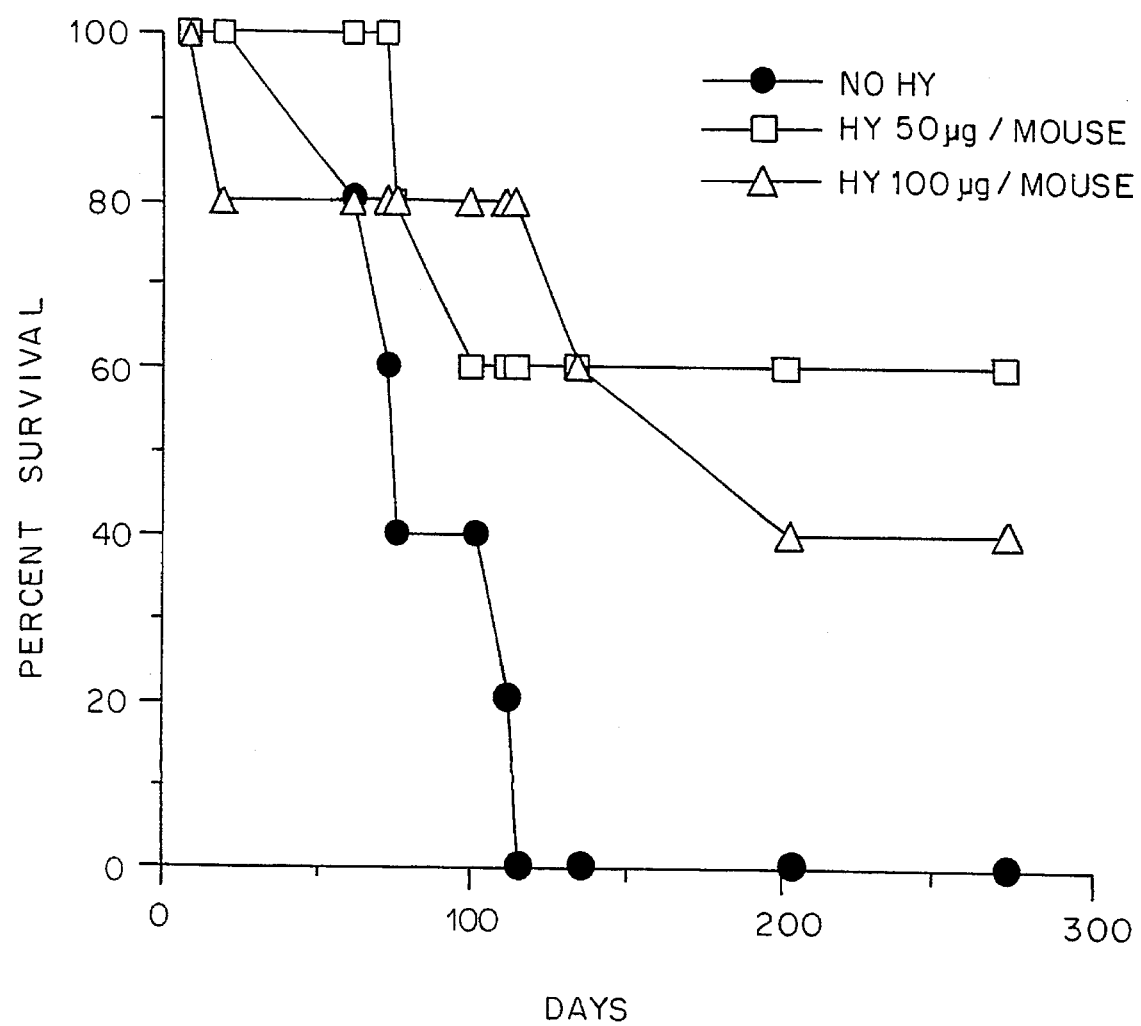
FIG. 11 is a graphical representation demonstrating the effect of 2x/week intraperitoneal injections of hypericin on C3H/lpr mice survival, followed up 273 days.
Figure 12:
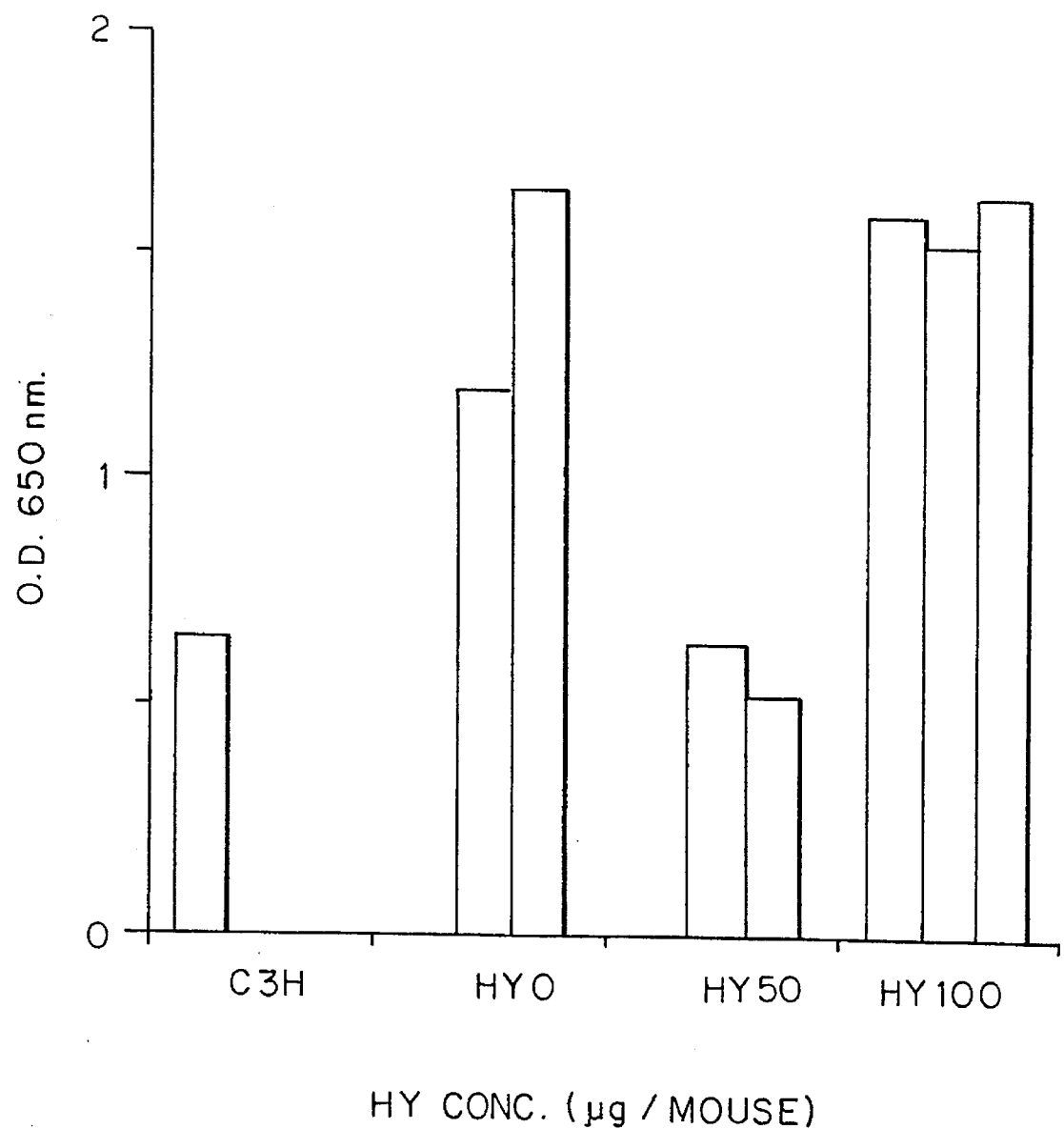
FIG. 12 is a graphical representation showing the effect intraperitoneal injections of hypericin on protein secretion in the urine (proteinuria in C3H/lpr mice.

FIGS. 10–12 show further studies of the effects of hypericins on C3H/lpr mice provided as above, 0;5 and 100 µg HY per mouse were administered and treated mice showed excellent survival rates up to 273 days, while control mice died after 110–120 days, as shown in FIG. 11. Significantly decrease proteinuria relative to controls at 50 µg/mouse H4, comparable to normal levels found in normal C3H mice.

These results indicate that an autoimmune disease, due in part to T cell dysregulation and abnormal proliferation of certain subsets of T cells, mainly CD4$^+$CD8$^+$ immature type T cells, is diminished by continuous polycyclic aromatic dione treatment, also including significantly decreased proteinuria.

EXAMPLE VII

Effects of Hypericin on the Cell Surface Expression of CD4

The effects of hypericin treatment on cell surface molecules were investigated. Changes in the expression of such molecules may explain how cells protect themselves from potential toxic effects of hypericin-mediated singlet oxygen reactions. Furthermore, because of the importance of CD4 molecules in various phases of the immune response, including in autoimmune phenomenon, it was important to examine changes induced by hypericin in CD4 expression.

Figure 7:
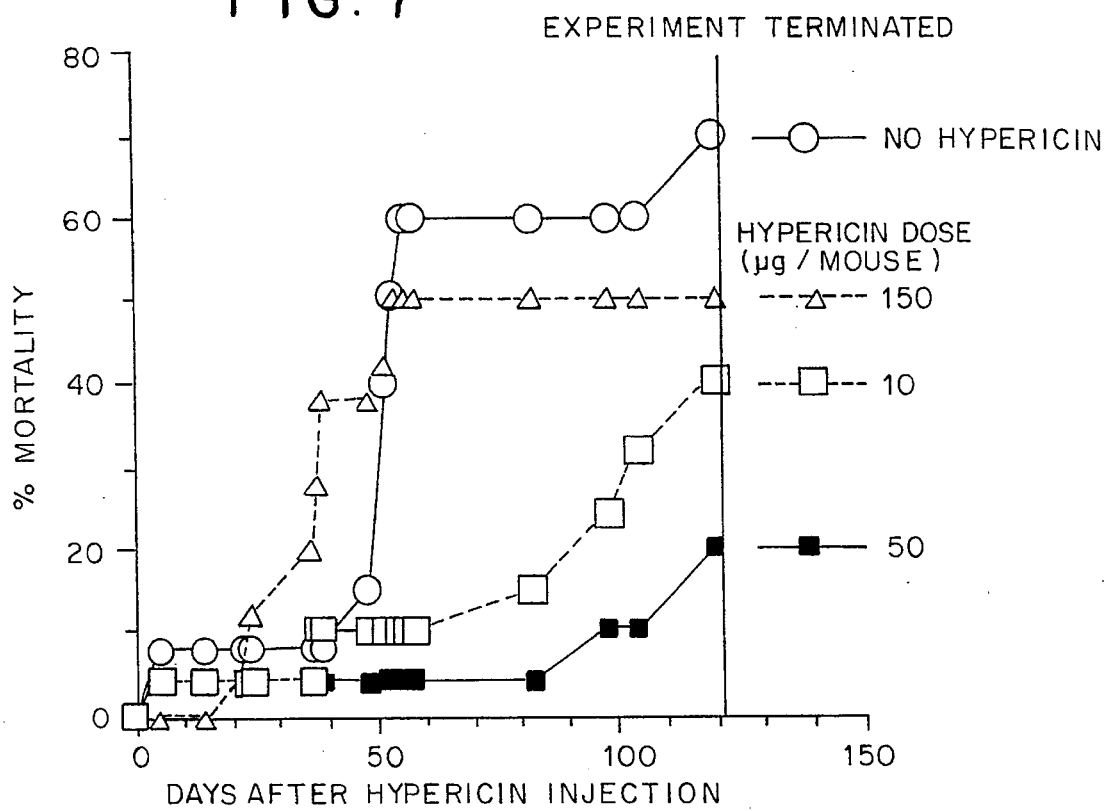
FIG. 7 is a graph showing enhanced survival of autoimmune mice of the MRL(lpr/lpr) strain in response to twice weekly treatment with hypericin at various doses.

Cells of a human T cell leukemia line, Supt-1, were incubated with varying concentrations of hypericin overnight. Following this incubation, the cells were subjected to flow cytometric analysis using fluorescein-labeled anti-CD4 antibodies (Becton-Dickinson). FIG. 7 shows that CD4 expression, measured as mean fluorescence intensity, decreased in proportion to increasing concentrations of hypericin. Thus, one mechanism by which hypericin acts is the diminution of expression of CD4 on the T cell surface.

EXAMPLE VII

Induction by Hypericin of Multidrug Resistance

In an attempt to render cells more resistant to the toxic action of hypericin, cells have been adapted gradually and progressively to continuous growth in increasing concentrations of hypericin for up to several months.

Figure 8:
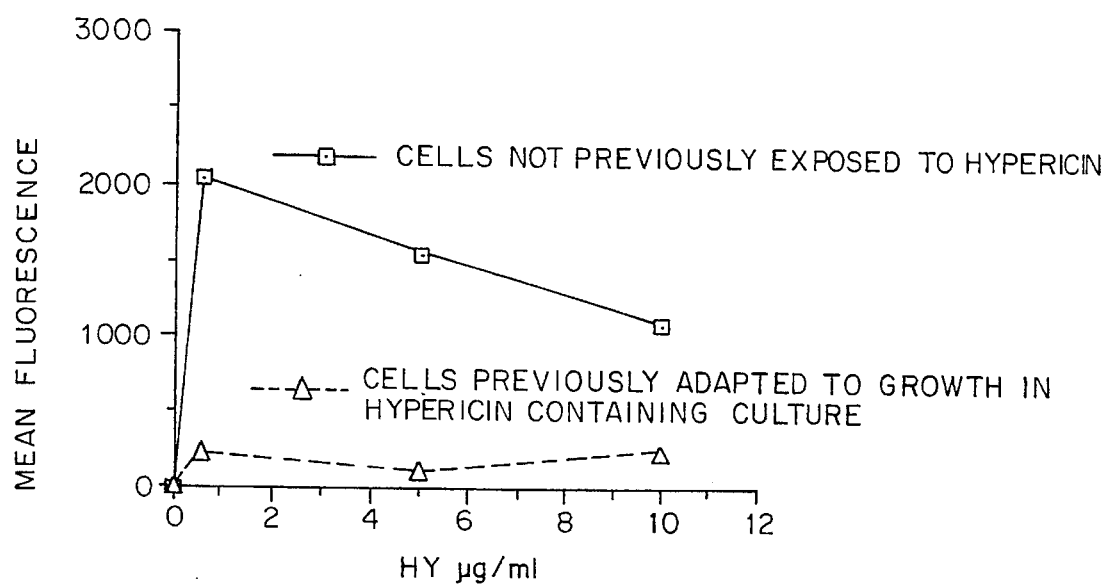
FIG. 8 is a graph showing that T cells (murine AQR line) adapted to growth in hypericin have a greatly reduced ability to take up hypericin after acute exposure.

Cells of the murine T cell line, AQR, grown continuously in the presence of hypericin, were washed free of hypericin and cultured in its absence for the final 24 hours before testing. These cells, and control AQR cells, were pulsed with hypericin at varying concentrations for 30 minutes, washed three times, and analyzed for uptake by examining their fluorescence using a FACS analyzer. The results are shown in FIG. 8. Cells which were adapted to growth in the presence of hypericin showed drastically reduced uptake of this compound.

Figure 9:
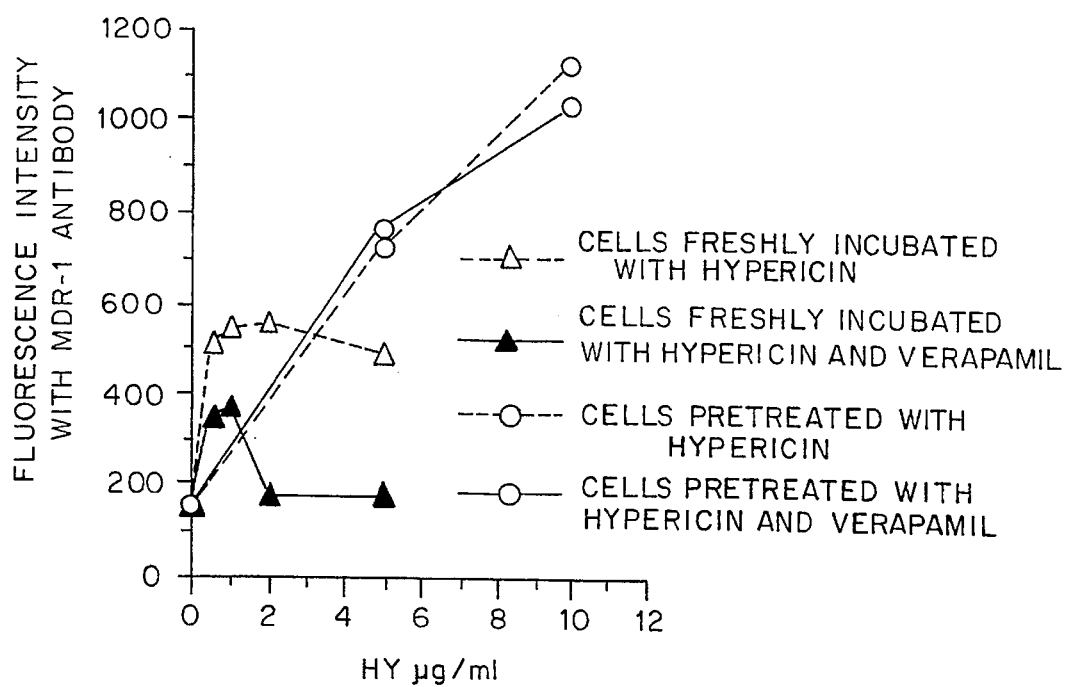
FIG. 9 is a graph showing the induction of a multidrug resistance glycoprotein by hypericin in AQR cells, and increased expression of this glycoprotein by cells adapted to growth in hypericin.

Experiments were conducted to examine whether this effect involved induction of higher levels of expression and/or production of multidrug resistance fmdr) glycoproteins. A monoclonal antibody specific for an mdr glycoprotein, MDR-1 (obtained from Oncogene Sciences), was used to examine cell surface expression of MDR-1. The results are shown in FIG. 9. Normal AQR cells, grown without hypericin, showed a hypericin-mediated induction of MDR-1, and were responsive to very low doses of hypericin. This induction was inhibited by the presence of 5 µg/ml verapamil. Verapamil is known to reverse the induction of mdr expression by various therapeutic drugs. In contrasts AQR cells which had adapted to growth in the presence of hypericin showed higher levels of MDR-1 glycoprotein expression which was not reversed by verapamil.

Thus, it is concluded that cells subjected to growth in the presence of hypericin take up less hypericin and develop mechanisms capable of actively excluding it following its uptake. Having now described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference hereins including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspects description or embodiment of the present invention is disclosed taught or suggested in the relevant art.

The foregoing description of the specific embodiments will so fully reveal the general nature of the invention that others cans by applying knowledge within the skill of the art (including the contents of the references cited herein), readily modify and/or adapt for various applications such specific embodiments, without undue experimentation, without departing from the general concept of the present invention. Therefores such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A method for treating a T cell-mediated disease in a mammal in need of such treatment, comprising administering to said mammal a T-cell inhibiting effective amount of at least one polycyclic aromatic dione compound or a salt thereof, wherein said disease is selected from the group consisting of graft versus host disease, graft rejection and an autoimmune disease.

2. A method according to claim 1, wherein said compound is selected from the group consisting of hypericin, pseudohypericin, desmethyl hypericin, hypericin diacetate, hypericin hexaacetate, hypericin methyl ester, hypericin propyl ester, isopropyl desmethyl hypericin, butyl ester of hypericic acid, sodium hypericin, potassium hypericin, lithium hypericin, hypericin-lysine, hypericin-glutamine, hypericin-ethylenediamine and hypericin-TRIS.

3. A method according to claim 2, wherein said compound is hypericin or pseudohypericin.

4. A method according to claim 1, wherein said disease is an autoimmune disease selected from the group consisting of multiple sclerosis, myasthenia gravis, systemic lupus erythematosus, scleroderma, polymyositis, Graves disease, Addison's disease, psoriasis, autoimmune uveoretinitis, autoimmune thyroidiris, Pemphigus vulgaris and rheumatoid arthritis.

5. A method according to claim 1, wherein said disease is graft-versus-host disease.

6. A method according to claim 1, wherein said disease is graft rejection.

* * * * *